United States Patent [19]

Kirst et al.

[11] 4,443,436

[45] Apr. 17, 1984

[54] C-20-MODIFIED MACROLIDE DERIVATIVES OF THE MACROLIDE ANTIBIOTICS TYLOSIN, DESMYCOSIN, MACROCIN, AND LACTENOCIN

[75] Inventors: Herbert A. Kirst; John E. Toth, both of Indianapolis, Ind.

[73] Assignee: Eli Lilly and Company, Indianapolis, Ind.

[21] Appl. No.: 417,248

[22] Filed: Sep. 13, 1982

[51] Int. Cl.$^3$ .................. A61K 31/71; C07H 17/08
[52] U.S. Cl. ................................. 424/180; 536/7.1
[58] Field of Search ................. 424/180; 536/7.1; 480/180

[56] References Cited

U.S. PATENT DOCUMENTS

| | | | |
|---|---|---|---|
| 3,178,341 | 4/1965 | Hamill et al. | 435/896 X |
| 3,326,759 | 6/1967 | Hamill et al. | 435/896 X |
| 4,196,280 | 4/1980 | Umezawa et al. | 536/7.1 |
| 4,268,665 | 5/1981 | Sakakibara et al. | 536/7.1 |
| 4,279,896 | 7/1981 | Ganguly et al. | 424/180 |
| 4,299,953 | 11/1981 | Hamill et al. | 536/7.1 |
| 4,321,361 | 3/1982 | Baltz et al. | 536/7.1 |
| 4,321,362 | 3/1982 | Baltz et al. | 536/7.1 |
| 4,345,069 | 8/1982 | Sakakibara et al. | 536/7.1 |
| 4,349,665 | 9/1982 | Lee et al. | 536/7.1 |
| 4,357,325 | 11/1982 | Ose et al. | 536/7.1 |

FOREIGN PATENT DOCUMENTS

| | | | |
|---|---|---|---|
| 53-21182 | 2/1978 | Japan | 536/7.1 |
| 53-130686 | 11/1978 | Japan | 536/7.1 |
| 53-132584 | 11/1978 | Japan | 536/7.1 |

OTHER PUBLICATIONS

Matsubara et al., "Chemical Transformation of Tylosin, a 16-Membered Macrolide and its Structure-Activity Relationship", *Chem. Pharm. Bull.* 30 (1), 97–110 (1982).

S. Omura et al., "Novel Dimeric Derivatives of Leucomycins and Tylosin, Sixteen-Membered Macrolides", *J. Med. Chem.* 25, 271–275 (1982).

Derwent Abstract No. 71396Y of Japanese Unexamined Patent 2100-485 (Takeda), Aug. 23, 1977.

A. Tanaka et al., "Syntheses of 4'-Deoxy-Demycarosyl Tylosin and Its Analogues", *J. Antibiotics* 34 (10), 1381–1384 (1981).

S. Satoi et al., "Mycinamicins, New Macrolide Antibiotics. I: Taxonomy, Production, Isolation, Characterization and Properties", *J. Antibiotics* 33 (4), 364–377 (1980).

*Primary Examiner*—Johnnie R. Brown
*Assistant Examiner*—Elli Peselev
*Attorney, Agent, or Firm*—Nancy J. Harrison; Arthur R. Whale

[57] ABSTRACT

C-20-Modified derivatives of the macrolide antibiotics tylosin, desmycosin, macrocin, lactenocin, 2'''-O-demethylmacrocin and 2''-O-demethyllactenocin inhibit pathogenic bacteria, especially gram-positive bacteria, Pasteurella species, and Mycoplasma species and pharmaceutical compositions thereof.

143 Claims, No Drawings

C-20-MODIFIED MACROLIDE DERIVATIVES OF THE MACROLIDE ANTIBIOTICS TYLOSIN, DESMYCOSIN, MACROCIN, AND LACTENOCIN

SUMMARY OF THE INVENTION

This invention relates to C-20-modified macrolide derivatives having formulas 1, 2, 3 and 4:

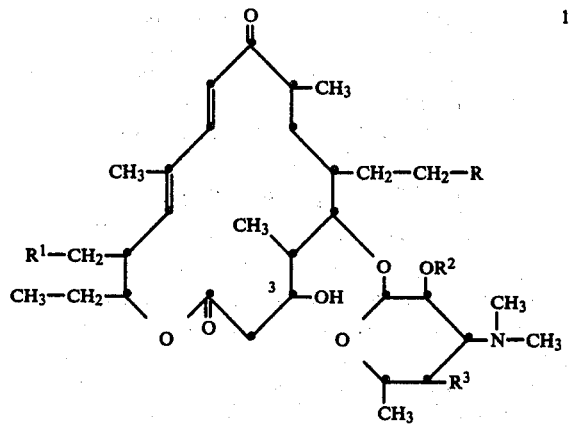

wherein

R is chloro, fluoro, —OR$^4$, —SR$^5$, —SO$_2$R$^6$, azido, —NHR$^7$, —N—phthalimido,

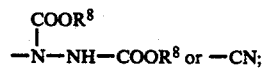

—N—NH—COOR$^8$ or —CN;

R$^1$ is

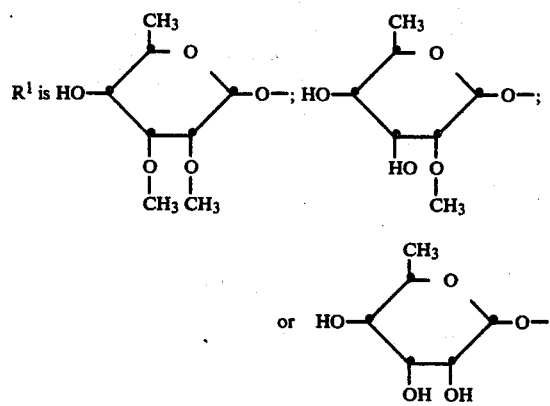

R$^2$ is hydrogen, optionally substituted C$_1$-C$_5$-alkanoyl or optionally substituted benzoyl, phenylacetyl or phenylpropionyl;

R$^3$ is hydroxy, optionally substituted C$_1$-C$_5$-alkanoyloxy, optionally substituted benzoyloxy, phenylacetoxy or phenoxyacetoxy or

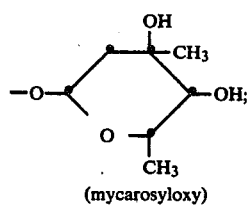

(mycarosyloxy)

R$^4$ is optionally substituted C$_1$-C$_4$-alkyl; cyclohexyl; optionally substituted benzyl, phenethyl or phenoxyethyl; phenyl; derivatized phenyl; naphthyl; an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; optionally substituted C$_1$-C$_5$-alkanoyl; optionally substituted benzoyl, phenylacetyl, phenylpropionyl, phenoxyacetyl or phenylthioacetyl; methanesulfonyl; trifluoromethanesulfonyl; optionally substituted phenylsulfinyl or phenylsulfonyl; cinoxacinyl; or —NO$_2$ (nitrate ester);

R$^5$ is optionally substituted C$_1$-C$_4$-alkyl; cyclohexyl; optionally substituted phenyl, benzyl or phenethyl; or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;

R$^6$ is optionally substituted C$_1$-C$_4$-alkyl or optionally substituted phenyl;

R$^7$ is hydrogen; optionally substituted C$_1$-C$_5$-alkanoyl; optionally substituted benzoyl, phenylacetyl, phenylpropionyl, phenoxyacetyl or phenylthioacetyl; or alkoxycarbonyl; and R$^8$ is methyl or ethyl;

provided that, when R$^7$ is hydrogen, R$^2$ must be hydrogen and R$^3$ must be hydroxy;

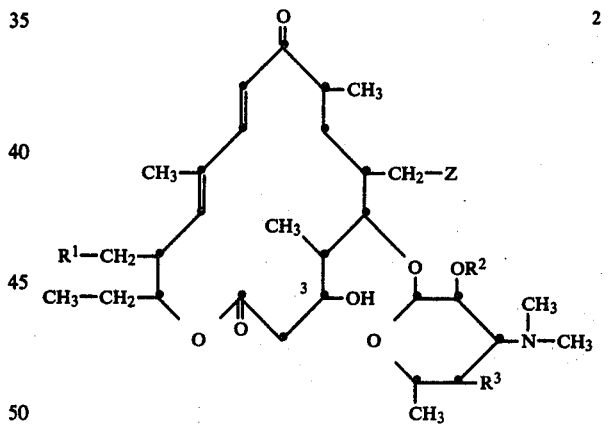

wherein

Z is hydrogen, methyl, —CH$_2$Br, —CH$_2$I or —CH$_2$O—(p-toluenesulfonyl);

R$^1$ is

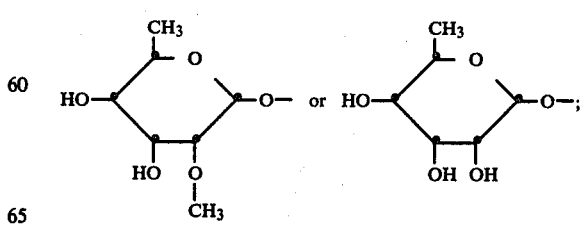

and
R$^2$ and R$^3$ are as defined in formula 1;

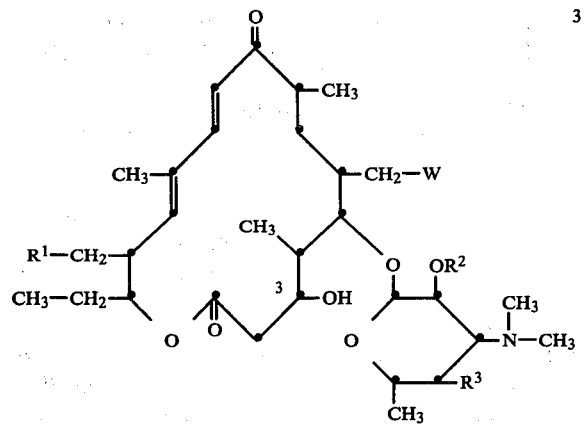

wherein
W represents

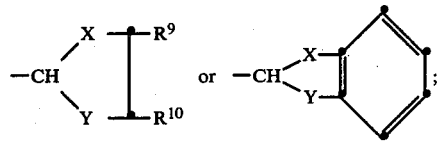

X and Y, independently, represent O, S, NH, N—CH₃, N-phenyl or N-benzyl;
$R^9$ and $R^{10}$, independently, are hydrogen, methyl, phenyl, methoxycarbonyl, ethoxycarbonyl or phenoxycarbonyl; and
$R^1$, $R^2$ and $R^3$ are as defined in formula 1;

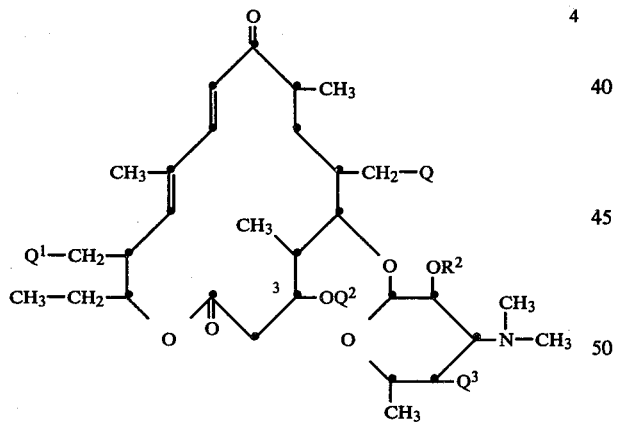

wherein
Q is —CH₂R or W;
$Q^1$ is

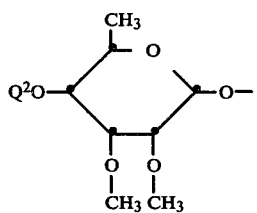

$Q^2$ is hydrogen or a hydroxyl-protecting group;

$Q^3$ is hydrogen or iodo;
R and $R^2$ are as defined in formula 1; and W is defined in formula 3; provided that all the $Q^2$ substituents must be identical and that $R^2$ must be hydrogen when $R^7$ is hydrogen; and to the acid addition salts of the compounds of formulas 1, 2, 3 and 4.

Although no stereochemical assignments have been indicated in the figures, the stereochemistry of the compounds of formulas 1-4 is that of tylosin.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-20-modified derivatives of the macrolide antibiotics tylosin, desmycosin, macrocin, lactenocin, 2'''-O-demethylmacrocin (DOMM) and 2''-O-demethyllactenocin (DOML) and to the acid addition salts of these derivatives. This invention also relates to methods of treating certain infections with, methods of promoting growth in animals with, and pharmaceutical compositions comprising the specified derivatives and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

One group of derivatives of this invention are compounds of formula 1:

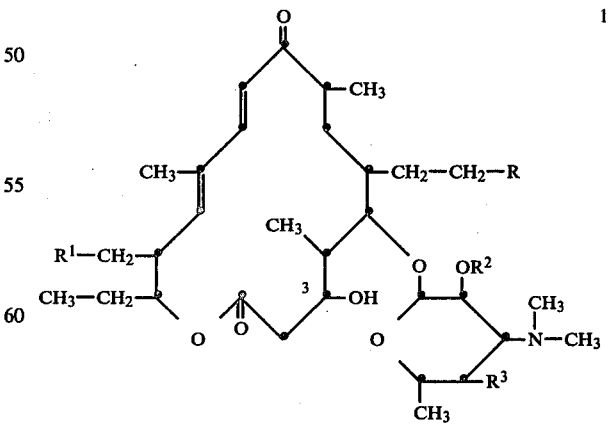

wherein
R is chloro, fluoro, —OR⁴, —SR⁵, —SO₂R⁶, azido, —NHR⁷, —N—phthalimido, $$\begin{array}{l}\phantom{-N-}COOR^8\\-N-NH-COOR^8 \text{ or } -CN;\end{array}$$

$R^1$ is 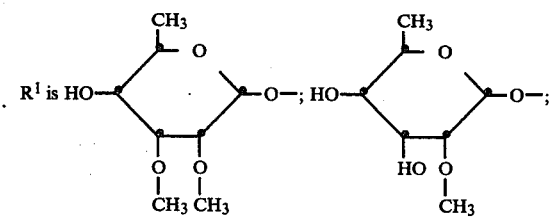

or 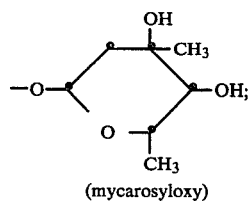

$R^2$ is hydrogen, optionally substituted $C_1$–$C_5$-alkanoyl or optionally substituted benzoyl, phenylacetyl or phenylpropionyl;

$R^3$ is hydroxy, optionally substituted $C_1$–$C_5$-alkanoyloxy, optionally substituted benzoyloxy, phenylacetoxy or phenoxyacetoxy or

[structure: mycarosyloxy]

(mycarosyloxy)

$R^4$ is optionally substituted $C_1$–$C_4$-alkyl; cyclohexyl; optionally substituted benzyl, phenethyl or phenoxyethyl; phenyl; derivatized phenyl; naphthyl; an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; optionally substituted $C_1$–$C_5$-alkanoyl; optionally substituted benzoyl, phenylacetyl, phenylpropionyl, phenoxyacetyl or phenylthioacetyl; methanesulfonyl; trifluoromethanesulfonyl; optionally substituted phenylsulfinyl or phenylsulfonyl, cinoxacinyl or —$NO_2$ (nitrate ester);

$R^5$ is optionally substituted $C_1$–$C_4$-alkyl; cyclohexyl; optionally substituted phenyl, benzyl or phenethyl or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;

$R^6$ is optionally substituted $C_1$–$C_4$-alkyl or optionally substituted phenyl;

$R^7$ is hydrogen; optionally substituted $C_1$–$C_5$-alkanoyl; optionally substituted benzoyl, phenylacetyl, phenylpropionyl, phenoxyacetyl or phenylthioacetyl; or alkoxycarbonyl; and $R^8$ is methyl or ethyl;

provided that, when $R^7$ is hydrogen, $R^2$ must be hydrogen and $R^3$ must be hydroxy;

and the acid addition salts of these compounds.

Another group of derivatives of this invention are compounds of formula 2:

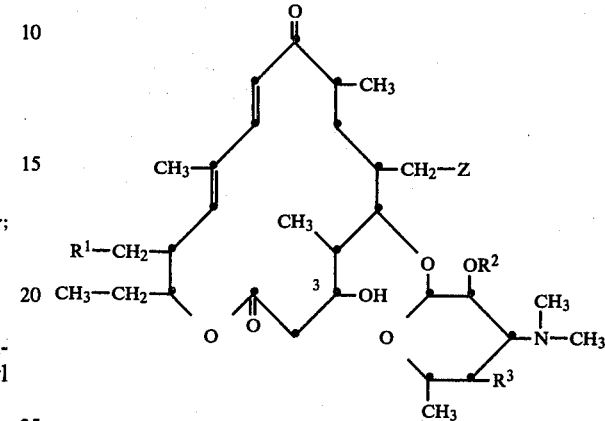

wherein

Z is hydrogen, methyl, —$CH_2Br$, —$CH_2I$ or —$CH_2O$—(p-toluenesulfonyl);

$R^1$ is

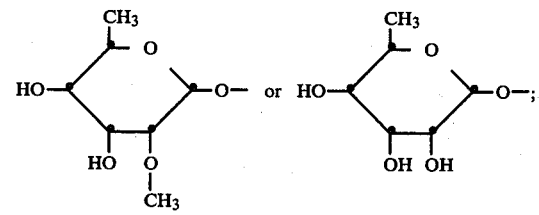

and $R^2$ and $R^3$ are as defined in formula 1; and the acid addition salts of these compounds.

A third group of compounds of this invention are compounds of formula 3:

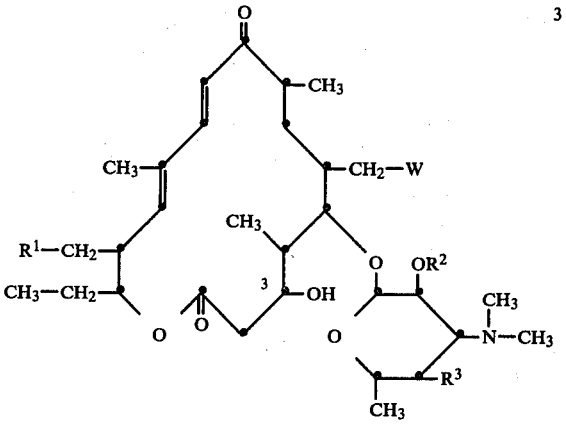

wherein

W represents

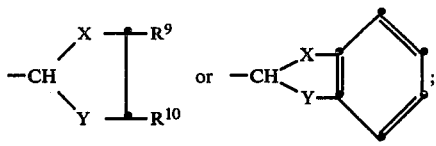

X and Y, independently, represent O, S, NH, N—CH₃, N-phenyl or N-benzyl;

R⁹ and R¹⁰, independently, are hydrogen, methyl, phenyl, methoxycarbonyl, ethoxycarbonyl or phenoxycarbonyl; and R¹, R² and R³ are as defined in formula 1; and the acid addition salts of these compounds.

A fourth group of compounds of this invention are the compounds of formula 4:

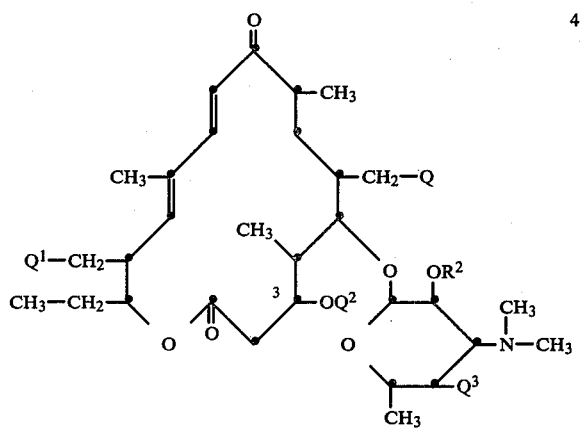

wherein
Q is —CH₂R or W;
Q¹ is

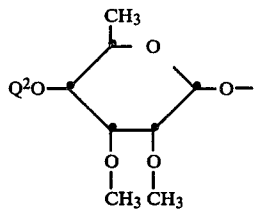

Q² is hydrogen or a hydroxyl-protecting group;
Q³ is hydrogen or iodo;
R and R² are as defined in formula 1; and W is defined in formula 3; provided that all the Q² substituents must be identical and that R² must be hydrogen when R⁷ is hydrogen; and the acid addition salts of these compounds.

The term "C₁–C₅-alkanoyl" as used herein refers to an acyl moiety derived from a carboxylic acid containing from one to five carbon atoms. In such a moiety, the alkyl group can be straight, branched, or cyclic. When optionally substituted, the alkyl group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups. The term "C₁–C₅-alkanoyloxy" refers to the corresponding acyloxy moiety.

The terms "optionally substituted benzoyl, phenylacetyl, phenylpropionyl, phenoxyacetyl or phenylthioacetyl", "optionally substituted benzoyl, phenylacetyl or phenylpropionyl", "optionally substituted benzoyloxy, phenylacetoxy or phenoxyacetoxy", "optionally substituted phenyl, benzyl or phenethyl", "optionally substituted benzyl, phenethyl or phenoxyethyl" and "optionally substituted phenyl" mean that the phenyl portion of the moiety is optionally substituted by from one to five halo or methyl groups or by from one to two methoxyl, nitro or hydroxyl groups.

The terms "optionally substituted phenylsulfinyl or phenylsulfonyl" mean that the phenyl portion of the moiety is optionally substituted by from one to five halo or from one to two nitro groups.

The term "derivatized phenyl" refers to a phenyl group which has from one to five halo, methoxyl or C₁–C₄-alkyl substituents, or from one to two nitro, amino, methylamino, ethylamino, dimethylamino, diethylamino, C₄–C₁₀-methyleneamino, azido, hydroxy, hydroxymethyl, aminomethyl, (methylamino)methyl, (ethylamino)methyl, (dimethylamino)methyl, (diethylamino)methyl, (C₄–C₇-methyleneamino)methyl, formyl, acetyl, benzoyl, methoxycarbonyl, ethoxycarbonyl, carboxamido, N-methylcarboxamido, N,N-dimethylcarboxamido, cyano, phenyl, phenoxy or benzyl substituents.

The term "optionally substituted heteroaryl group" as used herein means that the heteroaryl group may have at least one suitable substituent(s) such as a C₁–C₄-alkyl, halo, methoxy, ethoxy, hydroxy (or the keto tautomer) or phenyl group.

"Cinoxacinyl" refers to a 1-ethyl-1,4-dihydro-4-oxo[1,3]-dioxolo[4,5-g]cinnolin-3-yl group.

The term "C₁–C₄-alkyl" as used herein means a straight- or branched-chain alkyl group containing from one to four carbon atoms. Such groups include methyl, ethyl, isopropyl, n-butyl, tert-butyl, and the like. "Optionally substituted C₁–C₄-alkyl" refers to a C₁–C₄-alkyl group which contains one or more fluoro, chloro, bromo or iodo substituents on the alkyl group.

The R⁷ "alkoxycarbonyl" term represents a member of a group selected from t-butoxycarbonyl, methoxycarbonyl, ethoxycarbonyl, 2,2,2-trichloroethoxycarbonyl, phenoxycarbonyl and benzyloxycarbonyl.

The term "C₄–C₁₀-methyleneamino" represents a cyclic amino substituent of the formula —N(CH₂)ₙ wherein n is an integer from four to ten. Pyrrolidinyl, piperidinyl, and octahydroazocinyl are examples of such groups.

The term "hydroxyl-protecting group" refers to a substituent which is not removed under the reaction conditions but which can be readily removed after the reaction has been completed to liberate the original hydroxyl group. Hydroxyl-protecting groups are well known in the art (see, for example, T. W. Greene, "Protective Groups in Organic Synthesis", Wiley-Interscience, 1981, pp. 10–86). One especially suitable hydroxyl-protecting group is the tetrahydropyranyl group.

The C-20-modified macrolide derivatives of this invention are prepared from the group of macrolide antibiotics which includes tylosin, relomycin, desmycosin, 20-dihydrodesmycosin, macrocin, 20-dihydro-macrocin, 2‴-O-demethylmacrocin (DOMM), 20-dihydro-DOMM, lactenocin, 20-dihydro-lactenocin, 2″-O-demethyllactenocin (DOML) and 20-dihydro-DOML.

Tylosin and desmycosin are described by R. L. Hamill et al. in U.S. Pat. No. 3,178,341, issued Apr. 13, 1965.

Macrocin and lactenocin are described by Hamill et al. in U.S. Pat. No. 3,326,759, issued June 20, 1967. DOMM, dihydro-DOMM, DOML and dihydro-DOML are antibiotics described by Richard H. Baltz, Gene M. Wild, and Eugene T. Seno in copending application Ser. No. 169,051, filed July 15, 1980. The structures of these antibiotics are shown in formulas 5–16:

well exemplified in the art of nucleophilic substitution reactions.

The compounds of formula 2 wherein Z is hydrogen can be prepared by decarboxylation of the corresponding starting compound. Wilkinson's catalyst, i.e. chlorotris(triphenylphosphine)rhodium (I), is useful for this purpose [see A. J. Birch and D. H. Williamson, Org.

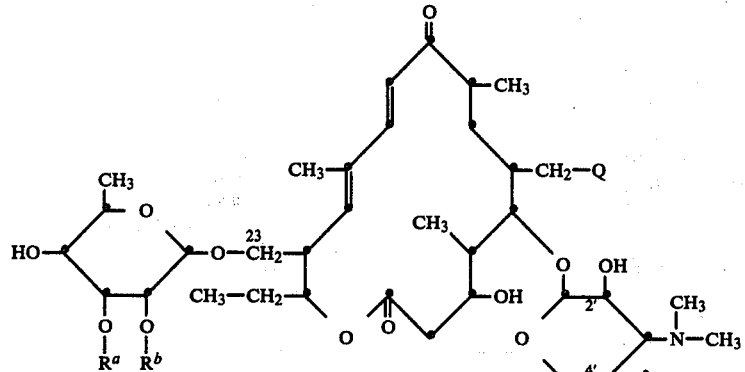

| | | Q | $R^a$ | $R^b$ | $R^3$ |
|---|---|---|---|---|---|
| 5 | (tylosin) | —CHO | —$CH_3$ | —$CH_3$ | —O—mycarosyl |
| 6 | (relomycin) | —$CH_2OH$ | —$CH_3$ | —$CH_3$ | —O—mycarosyl |
| 7 | (desmycosin) | —CHO | —$CH_3$ | —$CH_3$ | —OH |
| 8 | (dihydrodesmycosin) | —$CH_2OH$ | —$CH_3$ | —$CH_3$ | —OH |
| 9 | (macrocin) | —CHO | H | —$CH_3$ | —O—mycarosyl |
| 10 | (dihydromacrocin) | —$CH_2OH$ | H | —$CH_3$ | —O—mycarosyl |
| 11 | (lactenocin) | —CHO | H | —$CH_3$ | —OH |
| 12 | (dihydrolactenocin) | —$CH_2OH$ | H | —$CH_3$ | —OH |
| 13 | (DOMM) | —CHO | H | H | —O—mycarosyl |
| 14 | (dihydro-DOMM) | —$CH_2OH$ | H | H | —O—mycarosyl |
| 15 | (DOML) | —CHO | H | H | —OH |
| 16 | (dihydro-DOML) | —$CH_2OH$ | H | H | —OH |

Preparation of many of the C-20-modified derivatives of this invention involves first reducing the C-20 aldehyde group of tylosin, desmycosin, macrocin, lactenocin, DOMM or DOML to give the corresponding 20-dihydro-compounds of formulas 6, 8, 10, 12, 14 and 16. The C-20 hydroxyl group of these compounds may then be replaced by the desired substituent. Replacement can be accomplished by a variety of synthetic methodology. For example, one particularly useful method exemplified in this application is the diethylazodicarboxylate/triphenylphosphine system [see O. Mitsunobu, Synthesis 1(1), 1–28 (1981)].

The compounds of formulas 1 and 4 wherein R is chloro and the compounds of formula 2 wherein Z is —$CH_2Br$ or —$CH_2I$ may be conveniently prepared from the appropriate 20-dihydro compound using triphenylphosphine and a halogen source by methods well known in the art.

20-O-Carboxylate, sulfinate and sulfonate derivatives, e.g., compounds of formulas 1 and 4 wherein $R^4$ is an acyl, sulfinyl or sulfonyl moiety, may be prepared by acylation procedures well known in the art.

Compounds of formulas 1 and 4 wherein $R^4$ is methanesulfonyl, trifluoromethanesulfonyl or optionally substituted phenylsulfonyl, as well as compounds wherein the substituent represented by R in formula 1 may be iodo or bromo, are useful as intermediates for the preparation of additional compounds of this invention via $S_N1$ or $S_N2$ substitution reactions. Suitable reaction conditions for displacing a leaving group by a nucleophile via either an $S_N1$ or $S_N2$ mechanism are React. 24, 1 (1976)].

The C-20 derivatives wherein R is —$NHR^7$ are prepared via the 20-azido derivative (R=$N_3$). The 20-azido derivative is first reduced to the 20-amino derivative (R=$NH_2$); triphenylphosphine in aqueous tetrahydrofuran (THF) is an example of a suitable reducing agent for this purpose. The 20-amino derivative can then be selectively acylated on the amino group, using standard acylation procedures, to give those derivatives wherein $R^7$ is an acyl group.

The compounds of formula 3 are prepared by treating tylosin, desmycosin, macrocin, lactenocin, DOMM or DOML with a compound of formula 17 or 18:

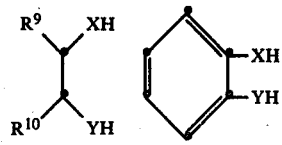

wherein X, Y, $R^9$ and $R^{10}$ are as herein defined, in a suitable solvent until derivatization of the aldehyde group is complete. In some cases, addition of an acidic catalyst or continuous removal of water may be necessary to drive the desired reaction to completion. Suitable reaction conditions for this transformation are known in the art and have been summarized in T. W.

Greene, "Protective Groups in Organic Synthesis", Wiley-Interscience, 1981, pp. 114–141.

The C-20-modified derivatives of desmycosin, lactenocin and DOML can also be prepared by acidic hydrolysis of mycarose from the corresponding C-20-modified derivatives of tylosin, macrocin and DOMM, respectively. Procedures for the acidic hydrolysis or mycarose from tylosin and macrocin to form desmycosin and lactenocin, respectively, are well known. DOMM is hydrolyzed in a similar manner to form DOML.

The 4'-deoxy derivatives of this invention, i.e. the compounds of formula 4, are readily prepared by procedures analogous to those described supra, using 4'-deoxydesmycosin as a starting material. The starting material can be prepared via procedures outlined in J. Antibiotics 34, 1381–1384 (1981). In many cases, the C-20-modified derivative of desmycosin can also be converted to the C-20-modified 4'-deoxy analog by similar procedures.

The ester derivatives of the C-20-modified compounds of this invention can be prepared by esterifying the corresponding C-20-modified derivative on the 2'- or 2',4'-hydroxyl groups by treatment with acylating agents, using standard methods well exemplified in the art. The preparation of 2'-O-ester derivatives of the C-20-modified derivatives is accomplished by procedures similar to those described by Baltz et al. in U.S. Pat. Nos. 4,321,361 and 4,321,362. 2',4'-Di-O-ester derivatives of C-20-modified derivatives may be prepared by procedures analogous to those described by Herbert A. Kirst in a co-pending application entitled OMT ESTER DERIVATIVES, Ser. No. 330,341, filed Dec. 4, 1981, which is incorporated herein by reference.

Alternatively, the esters of the C-20-modified derivatives can be prepared by starting with the corresponding ester derivatives of compounds 5–16, prepared as outlined, for example, in U.S. Pat. Nos. 4,321,361 and 4,321,362 and in Kirst application Ser. No. 330,341. The 20-substituent group of these esters can then be modified by the procedures described supra.

The C-20-modified derivatives of this invention form acid addition salts which are also useful as antibiotics and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

Illustrative C-20-modified derivatives of this invention are listed in Tables I–VIII.

TABLE I

| | Illustrative C-20 Modified Derivatives of Tylosin[a] | |
|---|---|---|
| Compound No. | R of Formula 1 | |
| 1 | N—phthalimido | |
| 2 | azido | |
| 3 | N—(phenylacetyl)amino | |
| 4 | phenoxy | |
| 5 | (1-methyltetrazol-5-yl)thio | |
| 6 | phenylthio | |
| 7 | chloro | |
| 8 | fluoro | |
| 9 | N—(ethoxycarbonyl), N—(ethoxycarbonylamino)-amino | |
| 10 | cinoxacinyloxy | |
| 11 | phenoxyacetoxy | |
| 12 | p-nitrophenoxy | |
| 13 | p-benzoylphenoxy | |
| 14 | p-methoxyphenoxy | |
| 15 | 3,5-dichlorophenoxy | |
| 16 | m-(N,N—dimethylamino)phenoxy | |
| 17 | p-formylphenoxy | |
| 18 | p-phenylphenoxy | |
| 19 | 2,2,2-trifluoro-1-(trifluoromethyl)ethoxy | |
| 19a | (quinaolin-4-yl)oxy | |

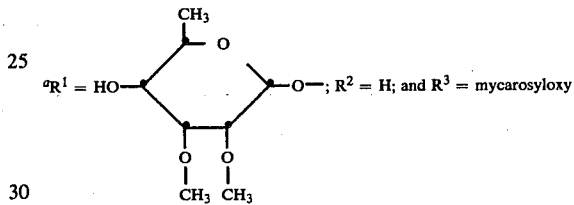

[a] $R^1 = HO-$ (structure shown); $R^2 = H$; and $R^3 = $ mycarosyloxy

TABLE II

| | Illustrative C-20 Modified Derivatives of Desmycosin[a] |
|---|---|
| Compound No. | R of Formula I |
| 20 | trifluoromethanesulfonyloxy |
| 21 | chloro |
| 22 | fluoro |
| 23 | phenylthio |
| 24 | (1-methyltetrazol-5-yl)thio |
| 25 | phenylsulfinyloxy |
| 26 | phenoxyacetoxy |
| 27 | cinoxacinyloxy |
| 28 | nitrato (ONO₂) |
| 29 | acetoxy |
| 30 | methoxy |
| 31 | 2-phenylethoxy |
| 32 | 2,2,2-trifluoro-1-(trifluoromethyl)ethoxy |
| 33 | phenoxy |
| 34 | p-nitrophenoxy |
| 35 | p-methoxyphenoxy |
| 36 | p-formylphenoxy |
| 37 | p-benzoylphenoxy |
| 38 | p-(ethoxycarbonyl)phenoxy |
| 39 | m-(N,N—dimethylamino)phenoxy |
| 40 | 3,5-dichlorophenoxy |
| 41 | p-phenylphenoxy |
| 42 | p-(hexahydroazepin-1-ylmethyl)phenoxy |
| 43 | N—phthalimido |
| 44 | azido |
| 45 | N—(ethoxycarbonyl), N—(ethoxycarbonylamino)amino |
| 46 | p-toluenesulfonyl |
| 47 | (p-phenoxy)phenoxy |
| 48 | (m-phenoxy)phenoxy |
| 49 | (pyridin-3-yl)oxy |
| 50 | (5,6-diphenyl-1,2,4-triazin-3-yl)oxy |
| 51 | (quinazolin-4-yl)oxy |
| 51a | p-(hydroxymethyl)phenoxy |
| 51b | amino |

TABLE II-continued

Illustrative C-20 Modified Derivatives of Desmycosin[a]

| Compound No. | R of Formula I |
|---|---|
| 51c | N—(phenoxyacetyl)amino |

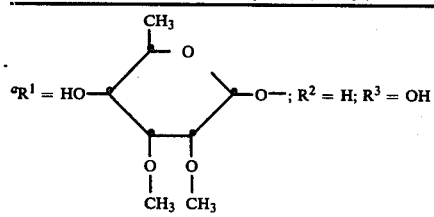

[a]$R^1$ = HO—[structure]—O—; $R^2$ = H; $R^3$ = OH

TABLE III

Illustrative C-20 Modified Derivatives of Macrocin[a]

| Compound No. | Z of Formula 2 | R of Formula 1 |
|---|---|---|
| 52 | —CH$_2$I | |
| 53 | | —O—[phenyl] |
| 54 | hydrogen | |
| 55 | methyl | |
| 56 | —CH$_2$O(p-toluenesulfonyl) | |

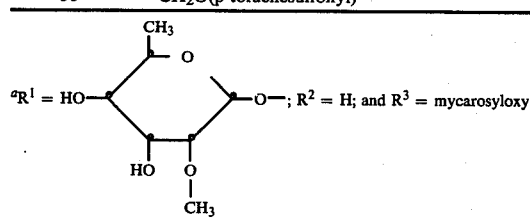

[a]$R^1$ = HO—[structure]—O—; $R^2$ = H; and $R^3$ = mycarosyloxy

TABLE IV

Illustrative C-20 Modified Derivatives of Lactenocin[a]

| Compound No. | Z of Formula 2 | R of Formula 1 |
|---|---|---|
| 57 | —CH$_2$I | |
| 58 | | —O—[phenyl] |
| 59 | hydrogen | |
| 60 | methyl | |
| 61 | —CH$_2$O(p-toluenesulfonyl) | |

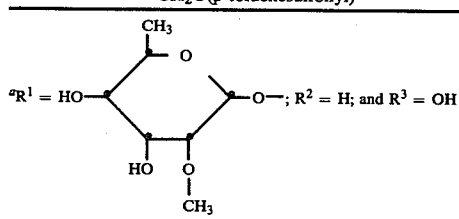

[a]$R^1$ = HO—[structure]—O—; $R^2$ = H; and $R^3$ = OH

TABLE V

Illustrative C-20-Modified Ester Derivatives of Tylosin[a]

| Compound No. | R | $R^2$ (2')[b] |
|---|---|---|
| 62 | N—phthalimido | propionyl |
| 63 | chloro | propionyl |

TABLE V-continued

Illustrative C-20-Modified Ester Derivatives of Tylosin[a]

| Compound No. | R | $R^2$ (2')[b] |
|---|---|---|
| 64 | phenoxy | acetyl |

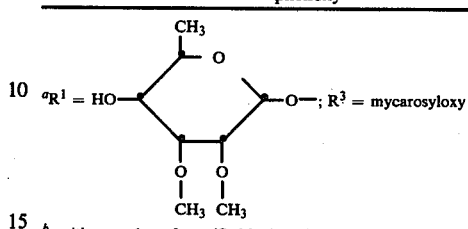

[a]$R^1$ = HO—[structure]—O—; $R^3$ = mycarosyloxy

[b]position number of esterified hydroxyl group in parentheses

TABLE VI

Illustrative C-20-Modified Ester Derivatives of Desmycosin[a]

| Compound No. | R | $R^2$ (2')[b] | $R^3$ (4') |
|---|---|---|---|
| 65 | N—phthalimido | propionyl | —OH |
| 66 | N—phthalimido | propionyl | —O—propionyl |
| 67 | phenoxy | acetyl | —OH |
| 68 | phenoxy | acetyl | —O—acetyl |
| 69 | chloro | propionyl | —OH |

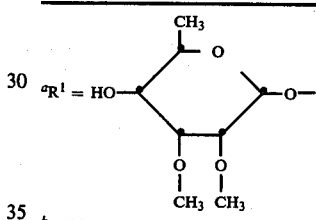

[a]$R^1$ = HO—[structure]—O—

[b]position number of esterified hydroxyl group in parentheses

TABLE VII

Illustrative C-20-Modified Derivatives of 4'-Deoxydesmycosin of Formula 4[a]

| Compound No. | R |
|---|---|
| 70 | phenoxy |
| 71 | chloro |
| 72 | N—phthalimido |
| 73 | hydrogen |

[a]Q = —CH$_2$R; $Q^1$ =

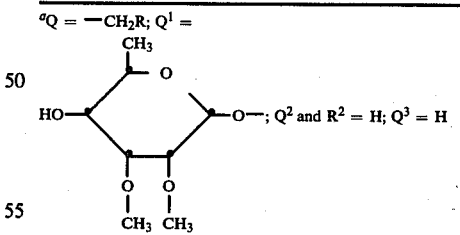

HO—[structure]—O—; $Q^2$ and $R^2$ = H; $Q^3$ = H

TABLE VIII

Illustrative C-20-Modified Derivatives of Desmycosin of Formula 3[a]

| Compound No. | W |
|---|---|
| 74 |  |

TABLE VIII-continued
Illustrative C-20-Modified Derivatives of Desmycosin of Formula 3[a]

| Compound No. | W |
|---|---|
| 75 | —CH(S-)(NH-) attached to benzene ring |
| 76 | —CH(S-)(NH-) with COOEt |
| 77 | —CH(S-)(N-CH₂-) attached to benzene ring |
| 78 | —CH(S-)(S-) (dithiolane) |
| 79 | —CH(O-)(N(CH₃)-) attached to benzene ring |
| 80 | —CH(O-CH₃)(S-CH₃) |

$^{a}R^1 = $ HO—[sugar ring with CH₃, O, O-CH₃, O-CH₃]—O—; $R^2 = $ H; R = OH

The derivatives of this invention inhibit the growth of pathogenic bacteria, especially gram-positive bacteria, Mycoplasma species and Pasteurella species. The derivatives are particularly useful against the Pasteurella species *P. multocida* and *P. hemolytica* and against *Mycoplasma hyopneumoniae*, the causative agent of mycoplasmal pneumonia in swine, and *Mycoplasma gallisepticum*.

In addition, many of the C-20-modified compounds of this invention exhibit higher blood levels than those of the parent compounds. For example, after oral administration of a single 15 mg/kg dose to female mongrel dogs, 20-DH-20-O-phenyl-desmycosin (Compound 33) gave a peak plasma level of 2.1 mcg/ml; whereas erythromycin gave 1.6 mcg/ml and desmycosin only gave 0.5 mcg/ml in analogous experiments.

The minimal inhibitory concentrations (MIC's) at which illustrative compounds inhibit certain bacteria are given in Tables IX and X. The MIC's in Table IX were determined by standard agar-dilution assays. The MIC's in Table X were obtained using conventional broth-dilution microtiter tests.

TABLE IX
Antibiotic Activity of C-20 Modified Derivatives[a]

| Test Organism | Test Compound[b] | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| *Staphylococcus aureus* X1.1 | 1 | 2 | 1 | 1 | 0.5 | 1 | 1 | 1 | 2 | 1 | 0.5 | 1 | 1 |
| *Staphylococcus aureus* V41[c] | 1 | 1 | 1 | 1 | 1 | 1 | 1 | 1 | 2 | 2 | 0.5 | 1 | 1 |
| *Staphylococcus aureus* X400[d] | 2 | 2 | 2 | 2 | 2 | 2 | 2 | 2 | 8 | 8 | 1 | 2 | 4 |
| *Staphylococcus aureus* S13E | 1 | 1 | 0.5 | 1 | 2 | 1 | 1 | 1 | 2 | 4 | 0.5 | 1 | 1 |
| *Staphylococcus epidermidis* EPI1 | 1 | 1 | 0.5 | 1 | 1 | 2 | 1 | 1 | 4 | 2 | 0.5 | 1 | 2 |
| *Staphylococcus epidermidis* EPI2 | 1 | NT | 0.5 | NT | NT | 1 | NT | 1 | 2 | 8 | 0.5 | 0.5 | 1 |
| *Streptococcus pyogenes* C203 | 2 | 2 | 2 | 2 | 1 | 4 | 2 | 4 | 16 | 1 | 0.5 | 2 | 2 |
| *Streptococcus pneumoniae* Park I | 32 | 32 | 1 | 32 | 32 | 64 | 32 | 64 | 2 | 0.5 | 0.5 | 16 | 1 |
| Streptococcus Group D X66 | NT[g] | 128 | 64 | 128 | 128 | — | — | — | — | 8 | 8 | 128 | 4 |
| Streptococcus Group 9960 | 128 | 128 | 64 | 128 | 128 | — | — | — | — | 8 | 8 | —[h] | 4 |
| *Haemophilus influenzae* Holt[e] | —[h] | — | 128 | — | — | — | — | — | — | 128 | — | — | — |
| *Haemophilus influenzae* R252[f] | — | — | 64 | — | 128 | — | — | 128 | — | 128 | — | 128 | — |

| | 14 | 15 | 16 | 17 | 18 | 19 | 19a | 21 | 22 | 23 | 24 | 25 | 26 | 27 |
|---|---|---|---|---|---|---|---|---|---|---|---|---|---|---|
| *Staphylococcus aureus* X1.1 | 0.5 | 1 | 1 | 1 | 2 | 4 | 0.5 | 0.25 | 0.25 | 0.25 | 0.5 | 0.25 | 0.25 | 2 |
| *Staphylococcus aureus* V41[c] | 0.5 | 2 | 1 | 1 | 2 | 4 | 0.5 | 0.12 | 0.25 | 0.25 | 0.5 | NT | 0.25 | 4 |
| *Staphylococcus aureus* X400[d] | 2 | 4 | 2 | 2 | 2 | 4 | 1 | 0.5 | 0.5 | 0.25 | 1 | 0.25 | 0.5 | 8 |
| *Staphylococcus aureus* S13E | 1 | 1 | 1 | 1 | 2 | 4 | 0.5 | 0.12 | 0.25 | 0.25 | 0.5 | 0.25 | 0.25 | 4 |
| *Staphylococcus epidermidis* EPI1 | 2 | 2 | 1 | 1 | 2 | 4 | 1 | 0.12 | 0.12 | 0.25 | 0.25 | 0.25 | 0.25 | 1 |
| *Staphylococcus epidermidis* EPI2 | 1 | 1 | 1 | 0.5 | 0.5 | 2 | 0.5 | NT[g] | 0.12 | 0.12 | NT | 0.12 | 0.12 | 4 |
| *Streptococcus pyogenes* C203 | 1 | 1 | 1 | 1 | 2 | 8 | 4 | 0.25 | 0.25 | 0.25 | 0.25 | 0.25 | 0.12 | 0.12 |
| *Streptococcus pneumoniae* Park I | 8 | 16 | 8 | 16 | 1 | 32 | 4 | 1 | 2 | 2 | 2 | NT | 0.12 | 0.12 |
| Streptococcus Group D X66 | 128 | — | 64 | 128 | 8 | — | 32 | 8 | 8 | 8 | 16 | 4 | 0.5 | 4 |
| Streptococcus Group 9960 | 128 | — | — | — | — | — | 64 | 8 | 8 | 16 | 32 | 4 | 0.5 | 8 |
| *Haemophilus influenzae* Holt[e] | 128 | — | 128 | — | — | — | 128 | 16 | 16 | 32 | 32 | 8 | 8 | 32 |
| *Haemophilus influenzae* R252[f] | — | — | — | — | — | — | — | 16 | 16 | 32 | 32 | 4 | 8 | 32 |

TABLE IX-continued

Antibiotic Activity of C-20 Modified Derivatives[a]

| Test Organism | Test Compound[b] | | | | | | | | | | | | | | |
|---|---|---|---|---|---|---|---|---|---|---|---|---|---|---|---|
| | 28 | 29 | 30 | 31 | 32 | 33 | 34 | 35 | 36 | 37 | 38 | 39 | 40 | 41 | 42 |
| *Staphylococcus aureus* X1.1 | 0.25 | 0.5 | 0.5 | 0.25 | 0.5 | 0.25 | 0.5 | 0.25 | 0.25 | 0.25 | 0.5 | 0.5 | 0.25 | 0.5 | 0.5 |
| *Staphylococcus aureus* V41[c] | 0.25 | 0.5 | 0.5 | 0.25 | 0.5 | 0.25 | 0.5 | 0.25 | 0.25 | 0.25 | 0.5 | 0.5 | 0.25 | 0.25 | 0.1 |
| *Staphylococcus aureus* X400[d] | 0.25 | 0.5 | 1 | 0.5 | 0.5 | 0.25 | 1 | 0.25 | 0.25 | 0.25 | 0.5 | 0.5 | 0.25 | 0.5 | 1 |
| *Staphylococcus aureus* S13E | 0.25 | 0.25 | 0.5 | 0.25 | 0.5 | 0.25 | 0.5 | 0.25 | 0.25 | 0.25 | 0.5 | 0.5 | 0.25 | 0.25 | 0.5 |
| *Staphylococcus epidermidis* EPI1 | 0.25 | 0.25 | 0.5 | 0.25 | 0.5 | 0.25 | 0.5 | 0.25 | 0.25 | 0.25 | 0.5 | 0.5 | 0.25 | 0.5 | 0.5 |
| *Staphylococcus epidermidis* EPI2 | 0.25 | 0.12 | 0.5 | 0.12 | 0.25 | 0.12 | 0.12 | 0.12 | 0.12 | 0.12 | 0.25 | 0.25 | 0.12 | 0.25 | 0.25 |
| *Streptococcus pyogenes* C203 | 0.25 | 2 | 0.5 | 1 | 0.5 | 2 | 1 | 1 | 1 | 0.06 | 0.5 | 0.25 | 0.12 | 0.25 | 0.5 |
| *Streptococcus pneumoniae* Park I | 2 | 0.25 | 4 | 0.25 | 4 | 2 | 1 | 1 | 1 | 0.06 | 1 | 1 | 1 | 0.25 | NT[g] |
| Streptococcus Group D X66 | 8 | 8 | 16 | 8 | 32 | 8 | 4 | 4 | 4 | 0.25 | 8 | 4 | 4 | 0.5 | 8 |
| Streptococcus Group 9960 | 8 | NT | 16 | 16 | 32 | 16 | 8 | 8 | 8 | 0.5 | 16 | 8 | 8 | 0.5 | 8 |
| *Haemophilus influenzae* Holt[e] | 16 | 16 | 32 | 32 | 64 | 32 | 16 | 32 | 16 | 16 | 16 | 32 | 32 | 16 | 32 |
| *Haemophilus influenzae* R252[f] | 16 | 16 | 32 | 32 | 128 | 32 | 16 | 16 | 16 | 16 | 32 | 16 | 16 | 16 | 32 |

| Test Organism | 43 | 44 | 45 | 46 | 47 | 48 | 49 | 50 | 51 | 51a | 51b | 51c | 52 | 53 |
|---|---|---|---|---|---|---|---|---|---|---|---|---|---|---|
| *Staphylococcus aureus* X1.1 | 0.12 | 0.12 | 0.5 | 0.25 | 0.5 | 0.5 | 0.5 | 0.5 | 0.25 | 0.5 | 4 | 0.25 | 2 | 2 |
| *Staphylococcus aureus* V41[c] | 0.12 | 0.12 | 0.5 | 0.25 | 0.5 | 0.5 | 0.5 | 0.5 | 0.25 | 0.5 | 4 | 0.25 | 2 | 2 |
| *Staphylococcus aureus* X400[d] | 0.5 | 0.25 | 1 | 0.25 | 0.5 | 0.5 | 0.5 | 1 | 0.5 | 1 | 8 | 0.5 | 8 | 4 |
| *Staphylococcus aureus* S13E | 0.25 | 0.12 | 0.5 | 0.25 | 0.25 | 0.5 | 0.5 | 0.5 | 0.25 | 0.5 | 4 | 0.25 | 4 | 2 |
| *Staphylococcus epidermidis* EPI1 | 0.12 | 0.12 | 0.5 | 0.25 | 0.5 | 0.5 | 0.5 | 0.5 | 0.25 | 0.5 | 8 | 0.25 | 2 | 2 |
| *Staphylococcus epidermidis* EPI2 | 0.25 | NT | 0.25 | 0.12 | 0.25 | 0.25 | 0.25 | 0.5 | 0.12 | 0.25 | 2 | 0.12 | 2 | 2 |
| *Streptococcus pyogenes* C203 | 0.25 | 0.25 | 2 | 1 | 0.25 | 0.25 | 2 | 0.5 | 0.5 | 0.5 | NT | 0.25 | 4 | 4 |
| *Streptococcus pneumoniae* Park I | 2 | 2 | 0.5 | 1 | 0.25 | 0.25 | 2 | 0.5 | 0.5 | NT | 16 | 0.25 | 16 | 32 |
| Streptococcus Group D X66 | NT | 4 | 16 | 8 | 0.5 | 0.5 | 16 | 4 | 4 | 16 | 128 | 1 | 128 | —[h] |
| Streptococcus Group 9960 | 4 | 8 | 8 | 8 | 1 | 1 | 16 | 4 | 4 | 16 | 128 | 1 | 128 | — |
| *Haemophilus influenzae* Holt[e] | 32 | 16 | 32 | 4 | 16 | 16 | 16 | 64 | 16 | 64 | 128 | 8 | — | — |
| *Haemophilus influenzae* R252[f] | 32 | 4 | 32 | 8 | 16 | 16 | 16 | 64 | 32 | 32 | — | 8 | — | — |

| Test Organism | 54 | 57 | 58 | 60 | 62 | 63 | 64 | 65 | 66 | 67 | 68 | 69 | 70 | 74 | 75 |
|---|---|---|---|---|---|---|---|---|---|---|---|---|---|---|---|
| *Staphylococcus aureus* X1.1 | 2 | 0.5 | 0.25 | 0.25 | 1 | 1 | 2 | 0.5 | 0.5 | 0.25 | 0.5 | 0.25 | 0.25 | 0.5 | 0.25 |
| *Staphylococcus aureus* V41[c] | 1 | 0.5 | 0.25 | 0.25 | 1 | 1 | 2 | 0.5 | 0.5 | 0.25 | 0.5 | 0.25 | 0.25 | 1 | 0.25 |
| *Staphylococcus aureus* X400[d] | 2 | 1 | 0.25 | 0.5 | 2 | 2 | 4 | 0.5 | 1 | 0.5 | 0.5 | 0.5 | 0.25 | 2 | 0.5 |
| *Staphylococcus aureus* S13E | 2 | 0.5 | 0.25 | 0.25 | 1 | 1 | 2 | 0.5 | 0.5 | 0.25 | 0.5 | 0.25 | 0.25 | 0.5 | 0.25 |
| *Staphylococcus epidermidis* EPI1 | 2 | 0.5 | 0.25 | 0.25 | 1 | 1 | 2 | 0.25 | 0.5 | 0.25 | 0.5 | 0.25 | 0.25 | 0.5 | 0.25 |
| *Staphylococcus epidermidis* EPI2 | 2 | 0.5 | 0.25 | 0.25 | 1 | 1 | 2 | NT | 0.25 | 0.12 | 0.12 | 0.12 | 0.12 | 0.25 | 0.12 |
| *Streptococcus pyogenes* C203 | 2 | 0.5 | 0.06 | NT | NT | 0.5 | 2 | 0.5 | 2 | 1 | 0.5 | 2 | 0.5 | NT | 0.5 |
| *Streptococcus pneumoniae* Park I | 64 | 4 | 0.25 | 0.5 | 2 | 16 | NT | 1 | 0.5 | 0.25 | 0.5 | 0.25 | 0.5 | 0.25 | 0.25 |
| Streptococcus Group D X66 | 128 | 16 | 4 | 8 | — | — | — | 8 | 8 | 4 | 4 | 8 | 2 | 8 | 2 |
| Streptococcus Group 9960 | 28 | 16 | 8 | 8 | — | — | — | 8 | 8 | 8 | 8 | 8 | 4 | 8 | 2 |
| *Haemophilus influenzae* Holt[e] | — | NT[g] | 32 | 32 | — | — | — | 64 | 64 | 32 | 32 | 16 | 4 | 32 | 16 |
| *Haemophilus influenzae* R252[f] | — | NT | 16 | 16 | — | — | — | 32 | 64 | 16 | 16 | 16 | 4 | 32 | 16 |

| Test Organism | 76 | 77 |
|---|---|---|
| *Staphylococcus aureus* X1.1 | 0.5 | 0.25 |
| *Staphylococcus aureus* V41[c] | 0.5 | 0.25 |
| *Staphylococcus aureus* X400[d] | 2 | 0.25 |
| *Staphylococcus aureus* S13E | 0.5 | 0.25 |
| *Staphylococcus epidermidis* EPI1 | 0.5 | 0.25 |
| *Staphylococcus epidermidis* EPI2 | 0.25 | 0.12 |
| *Streptococcus pyogenes* C203 | 0.5 | 0.25 |
| *Streptococcus pneumoniae* Park I | 0.25 | 1 |
| Streptococcus Group D X66 | 4 | 4 |
| Streptococcus Group 9960 | 4 | 4 |
| *Haemophilus influenzae* Holt[e] | 32 | 16 |
| *Haemophilus influenzae* R252[f] | 32 | 16 |

[a]MIC in mcg/ml
[b]Compound numbers from Tables I-VIII
[c]Penicillin-resistant strain
[d]Methicillin-resistant strain
[e]Ampicillin-sensitive strain
[f]Ampicillin-resistant strain
[g]Not tested
[h]Not active at 128 mcg/ml, the highest level tested

TABLE X

Antibiotic Activity of C-20 Modified Derivatives[a]

| Test Organism | Test Compound[b] | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| *Staphylococcus aureus* | 6.25 | 3.12 | 1.56 | 3.12 | 1.56 | 3.12 | 3.12 | 1.56 | 6.25 | 12.5 | 1.56 | 1.56 | 1.56 | 1.56 | 1.56 | 1.56 |
| *Streptococcus bovis* 80 | 50 | 50 | 6.25 | 12.5 | — | — | 12.5 | — | — | 3.12 | 3.12 | 25 | 1.56 | 25 | 6.25 | 50 |
| *Pasteurella multocida* 17E[c] | —[e] | — | — | — | — | — | — | — | — | —[e] | — | — | — | — | — | — |
| *Pasteurella multocida* 60A[d] | — | — | — | — | — | — | — | — | — | — | — | — | — | — | — | — |
| *Pasteurella hemolytica* 22C | — | — | — | — | — | — | — | — | — | — | — | — | — | — | — | — |
| *Mycoplasma gallisepticum* | 3.12 | 1.56 | 0.78 | 1.56 | 1.56 | 0.78 | 0.78 | 1.56 | 1.56 | 0.78 | 1.56 | 0.39 | 0.78 | 0.78 | 1.56 | 1.56 |
| *Mycoplasma synoviae* | 6.25 | 12.5 | NT[f] | NT | 3.12 | 12.5 | NT | 12.5 | 25 | NT[f] | 3.12 | 1.56 | 6.25 | 6.25 | 3.12 | 6.25 |
| *Mycoplasma hyorhinis* | — | — | 12.5 | 50 | — | — | 50 | — | — | 25 | — | 50 | 6.25 | — | 50 | 50 |

TABLE X-continued

Antibiotic Activity of C-20 Modified Derivatives[a]

| Test Organism | | | | | | | | | | | | | | | |
|---|---|---|---|---|---|---|---|---|---|---|---|---|---|---|---|
| Mycoplasma hyopneumoniae | NT | NT | NT | NT | NT | >25 | NT | >25 | NT | NT | NT | >25 | 3.12 | >25 | >25 | >25 |

| | | | | | | | Test Compound[b] | | | | | | | | |
|---|---|---|---|---|---|---|---|---|---|---|---|---|---|---|---|
| Test Organism | 17 | 19 | 21 | 22 | 23 | 24 | 25 | 26 | 27 | 28 | 29 | 30 | 32 | 33 | 34 |
| Staphylococcus aureus | 1.56 | 12.5 | 0.78 | 3.12 | 0.19 | 0.78 | 0.39 | 0.39 | 3.12 | 1.56 | 0.78 | 0.78 | 0.78 | 0.39 | 0.39 |
| Streptococcus bovis 80 | 50 | — | 3.12 | 1.56 | 6.25 | 12.5 | 3.12 | 1.56 | 0.78 | 12.5 | 0.78 | 12.5 | 12.5 | 6.25 | 1.56 |
| Pasteurella multocida 17E[c] | — | — | 12.5 | 25 | 12.5 | 12.5 | 12.5 | 6.25 | 25 | 25 | 12.5 | 25 | 50 | 12.5 | 12.5 |
| Pasteurella multocida 60A[d] | — | — | 6.25 | 25 | 12.5 | 12.5 | 6.25 | 6.25 | 25 | 50 | 25 | 25 | 50 | 12.5 | 25 |
| Pasteurella hemolytica 22C | — | — | 12.5 | —[e] | 25 | 12.5 | 12.5 | 12.5 | 50 | 25 | 25 | 25 | 50 | 25 | 25 |
| Mycoplasma gallisepticum | 0.78 | 3.12 | 0.39 | 12.5 | 0.09 | 1.56 | <0.05 | <0.05 | 1.56 | 0.78 | 0.39 | 0.39 | 0.19 | 0.39 | 0.39 |
| Mycoplasma synoviae | 6.25 | 12.5 | NT[f] | 50 | 6.25 | 0.78 | 0.19 | 1.56 | NT | 0.78 | 1.56 | 0.39 | 1.56 | 1.56 | 0.78 |
| Mycoplasma hyorhinis | — | — | 50 | 50 | — | 50 | — | 50 | 6.25 | 50 | 50 | 50 | —[e] | 25 | 50 |
| Mycoplasma hyopneumoniae | >25 | >25 | 12.5 | >25 | >25 | 12.5 | 12.5 | 0.78 | NT | NT | 12.5 | 12.5 | >25 | 25 | 12.5 |

| | | | | | | | Test Compound[b] | | | | | | | | |
|---|---|---|---|---|---|---|---|---|---|---|---|---|---|---|---|
| Test Organism | 35 | 36 | 37 | 38 | 39 | 40 | 41 | 42 | 43 | 44 | 45 | 46 | 47 | 48 | 49 |
| Staphylococcus aureus | 0.39 | 12.5 | 0.19 | 0.78 | 6.25 | 0.39 | 0.19 | 1.56 | 0.78 | 0.39 | 1.56 | 0.39 | 0.78 | 0.78 | 1.56 |
| Streptococcus bovis 80 | 1.56 | 12.5 | 0.19 | 0.78 | 1.56 | 3.12 | 0.39 | 3.12 | 6.25 | 6.25 | 12.5 | 6.25 | 0.09 | 0.09 | 25 |
| Pasteurella multocida 17E[c] | 12.5 | 25 | 12.5 | 25 | 25 | 12.5 | 12.5 | 12.5 | 25 | 6.25 | 25 | 12.5 | 25 | 25 | 25 |
| Pasteurella multocida 60A[d] | 12.5 | 12.5 | 25 | 50 | 12.5 | 12.5 | 12.5 | 12.5 | 12.5 | 6.25 | 25 | 12.5 | 25 | 25 | 25 |
| Pasteurella hemolytica 22C | 25 | 50 | 12.5 | 50 | — | 12.5 | 25 | 12.5 | 25 | 12.5 | 50 | 12.5 | 25 | 25 | 25 |
| Mycoplasma gallisepticum | 0.39 | 25 | 0.19 | 0.39 | 1.56 | <0.05 | <0.05 | 0.39 | 0.78 | 0.39 | 0.39 | 0.19 | <0.05 | <0.05 | 0.78 |
| Mycoplasma synoviae | 0.78 | — | 1.56 | 1.56 | 1.56 | 0.19 | 0.39 | 0.195 | 0.78 | NT | 6.25 | 0.78 | 0.09 | 0.19 | 3.12 |
| Mycoplasma hyorhinis | — | 50 | 0.78 | 25 | 25 | 12.5 | 3.12 | 25 | 50 | 50 | —[e] | 50 | 6.25 | 12.5 | 50 |
| Mycoplasma hyopneumoniae | 6.25 | 12.5 | 0.19 | NT | 6.25 | 12.5 | 3.12 | NT[f] | 12.5 | 6.25 | 6.25 | 12.5 | 3.12 | 1.56 | 25 |

| | | | | | | | Test Compound[b] | | | | | | | | |
|---|---|---|---|---|---|---|---|---|---|---|---|---|---|---|---|
| Test Organism | 50 | 51 | 52 | 53 | 54 | 56 | 57 | 58 | 60 | 62 | 63 | 64 | 65 | 66 | 67 |
| Staphylococcus aureus | 1.56 | 0.78 | 12.5 | 0.39 | 3.12 | 3.12 | 0.78 | 0.39 | 0.78 | 3.12 | 6.25 | 3.12 | 1.56 | 0.78 | 0.78 |
| Streptococcus bovis 80 | 3.12 | 0.78 | 50 | 6.25 | 6.25 | 6.25 | 3.12 | 1.56 | 6.25 | 12.5 | 25 | 12.5 | 6.25 | 6.25 | 12.5 |
| Pasteurella multocida 17E[c] | 25 | 12.5 | — | 25 | — | — | 25 | 25 | 25 | —[e] | — | — | 25 | 25 | 25 |
| Pasteurella multocida 60A[d] | 25 | 12.5 | — | 12.5 | — | — | 25 | 12.5 | 25 | — | — | — | 12.5 | 25 | 25 |
| Pasteurella hemolytica 22C | —[e] | — | — | 25 | — | — | 25 | 25 | 25 | — | — | — | 25 | 25 | 25 |
| Mycoplasma gallisepticum | ≦0.048 | ≦0.048 | 3.12 | <0.05 | 0.78 | 1.56 | 3.12 | 0.78 | 1.56 | 1.56 | 1.56 | 1.56 | <0.05 | 0.09 | 0.39 |
| Mycoplasma synoviae | 0.39 | 0.39 | NT | 3.12 | 1.56 | 12.5 | 1.56 | 6.25 | — | NT[f] | NT | NT | NT | NT | 3.12 |
| Mycoplasma hyorhinis | 12.5 | 12.5 | 50 | 50 | 25 | — | 50 | 50 | 50 | 50 | 50 | 50 | — | 50 | 50 |
| Mycoplasma hyopneumoniae | NT[f] | NT | NT | 0.78 | NT | NT | NT | 6.25 | NT | NT | NT | NT | 12.5 | 25 | 12.5 |

| | Test Compound[b] | | | | | | |
|---|---|---|---|---|---|---|---|
| Test Organism | 68 | 69 | 70 | 74 | 75 | 76 | 77 |
| Staphylococcus aureus | 0.39 | 0.78 | 0.78 | 3.12 | 0.78 | 0.78 | 0.39 |
| Streptococcus bovis 80 | 6.25 | 6.25 | 6.25 | 6.25 | 3.12 | 3.12 | 3.12 |
| Pasteurella multocida 17E[c] | 25 | 25 | 12.5 | 25 | 25 | 25 | 12.5 |
| Pasteurella multocida 60A[d] | 25 | 2.5 | 12.5 | 50 | 25 | 25 | 12.5 |
| Pasteurella hemolytica 22C | 25 | 25 | 50 | 50 | 25 | 25 | 12.5 |
| Mycoplasma gallisepticum | 0.39 | 0.39 | 0.39 | 3.12 | 1.56 | 1.56 | 0.09 |
| Mycoplasma synoviae | 3.12 | NT | 0.78 | 6.25 | 1.56 | 3.12 | 0.19 |
| Mycoplasma hyorhinis | — | 50 | 12.5 | 50 | 50 | 50 | 6.25 |
| Mycoplasma hyopneumoniae | 12.5 | 12.5 | 6.25 | 1.56 | 0.19 | 0.19 | 0.19 |

[a]MIC in mcg/ml
[b]Compound numbers from Tables I–VIII
[c]Bovine isolate
[d]Avian isolate
[e]Not active at 50 mcg/ml, the highest level tested
[f]Not tested The C-20 modified derivatives of this invention have shown in vivo antimicrobial activity against experimentally-induced infections in laboratory animals. When two doses of test compound were administered to mice experimentally infected with S. pyogenes C203, the activity observed was measured as an ED$_{50}$ value [effective dose in mg/kg to protect 50% of the test animals: see Warren Wick, et al., J. Bacteriol. 81, 233–235 (1961)]. ED$_{50}$ values observed for illustrative compounds are given in Table XI.

TABLE XI

ED$_{50}$ Values of C-20-Modified Derivatives[a]

| | Streptococcus pyogenes C203 | |
|---|---|---|
| Test Compound[b] | Subcutaneous | Oral |
| 1 | >6.3 | 71 |
| 2 | >6.3 | 18 |
| 4 | >6.3 | 35 |
| 5 | >6.3 | 56 |
| 7 | >6.3 | 11 |
| 21 | 0.7 | 6 |
| 22 | 5.0 | 11 |
| 23 | 10.0 | 17 |
| 24 | 2.4 | 50 |
| 25 | 5.0 | 45 |
| 26 | 2.4 | >25 |
| 27 | <1.5 | >100 |
| 29 | 3.4 | 36 |
| 30 | >6.3 | 25 |
| 32 | >10 | 25 |
| 33 | 1.5 | 9 |
| 34 | 1.1 | 5 |
| 35 | 1.6 | 11 |
| 36 | 2.2 | 19 |
| 37 | 7.2 | 18 |
| 38 | >10 | 35 |
| 39 | 6.7 | 19 |

TABLE XI-continued

ED$_{50}$ Values of C-20-Modified Derivatives[a]

| Test Compound[b] | Streptococcus pyogenes C203 | |
|---|---|---|
| | Subcutaneous | Oral |
| 40 | >10 | 31 |
| 41 | >10 | 25 |
| 42 | >25 | >100 |
| 43 | 1.6 | 16 |
| 44 | 3.8 | 13 |
| 45 | 2.1 | >50 |
| 46 | 4.2 | >50 |
| 47 | >10 | 29 |
| 48 | >10 | 35 |
| 50 | >10 | >50 |
| 51 | 5.4 | >50 |
| 54 | NT[c] | 31 |
| 57 | 5.2 | 79 |
| 58 | 3.2 | 50 |
| 60 | 3.9 | 46 |
| 62 | >6.3 | 66 |
| 63 | >6.3 | 22 |
| 65 | 1.7 | 20 |
| 66 | >6.3 | 31 |
| 67 | 1.0 | 9 |
| 68 | 2.9 | 16 |
| 69 | 3.3 | 27 |
| 70 | 3.1 | 7 |
| 74 | 3.3 | >25 |
| 75 | 1.7 | 30 |
| 76 | 4.8 | 17 |
| 77 | >10 | 19 |

[a]mg/kg × 2; doses given 1 and 4 hours post-infection
[b]Compound numbers from Tables I-VIII
[c]Not tested Many of the C-20 modified derivatives of this invention have also shown in vivo antibacterial activity against infections induced by gram-negative bacteria. Tables XII and XIII summarize the results of tests in which illustrative compounds were evaluated against Pasteurella infection in one-day-old chicks. The compounds were administered parenterally or orally after challenge of the chicks with Pasteurella multocida (0.1 ml of a $10^{-4}$ dilution of a twenty-hour tryptose broth culture of an avian P. multocida given subcutaneously). In these tests, unless indicated otherwise, all non-medicated infected chicks died within 24 hours of Pasteurella challenge. In the tests summarized in Table XII the compounds were administered by subcutaneous injection at a dosage of 30 mg/kg, 1 and 4 hours post-challenge of the chicks with P. multocida. In the test summarized in Table XIII the compounds were administered by gavage at 1 and 5 hours post-challenge of the chicks with P. multocida.

TABLE XII

Activity of C-20-Modified Derivatives Administered Subcutaneously to Pasteurella multocida-Infected Chicks[a]

| Test Compound[b] | Number of Deaths/Number Treated |
|---|---|
| 21 | 9/10 |
| 21 | 7/10c |
| 24 | 2/10 |
| 24 | 0/10 |
| 26 | 8/10 |
| 27 | 6/10 |
| 29 | 5/10 |
| 30 | 10/10 |
| 33 | 10/10 |
| 43 | 10/10 |
| 44 | 9/10 |
| 45 | 9/10 |
| 46 | 0/10 |
| 49 | 9/10 |
| 75 | 4/10 |
| 76 | 3/10 |

TABLE XII-continued

Activity of C-20-Modified Derivatives Administered Subcutaneously to Pasteurella multocida-Infected Chicks[a]

| Test Compound[b] | Number of Deaths/Number Treated |
|---|---|
| 77 | 8/10[d] |

[a]Administered subcutaneously; 30 mg/kg × 2
[b]Compound numbers from Tables I-VIII
[c]8/10 infected non-medicated chicks died in this test
[d]8/10 and 9/10 of two groups of infected non-medicated chicks died in this test

TABLE XIII

Activity of C-20-Modified Derivatives Administered Orally to Pasteurella multocida-Infected Chicks[a]

| Test Compound[b] | Dose (g/gal)[c] | Number of Deaths/Number tested |
|---|---|---|
| 21 | 2.0 | 0/9 |
| 21 | 1.0 | 3/9 |
| 21 | 2.0 | 0/10 |
| 21 | 2.0 | 2/10[d] |
| 22 | 0.5 | 6/10 |
| 22 | 1.0 | 0/10 |
| 22 | 2.0 | 1/10 |
| 23 | 0.5 | 8/10 |
| 23 | 1.0 | 10/10 |
| 24 | 2.0 | 1/9 |
| 24 | 1.0 | 2/9 |
| 29 | 0.5 | 0/10 |
| 29 | 1.0 | 3/10 |
| 33 | 2.0 | 3/9 |
| 33 | 1.0 | 9/9 |
| 33 | 2.0 | 7/10[d] |
| 34 | 0.5 | 7/10 |
| 34 | 1.0 | 9/10 |
| 35 | 1.5 | 1/10 |
| 35 | 2.0 | 4/10 |
| 37 | 1.5 | 10/10 |
| 40 | 1.5 | 10/10 |
| 75 | 2.0 | 3/9 |
| 75 | 1.0 | 6/9 |
| 75 | 2.0 | 4/10 |
| 76 | 0.5 | 3/10 |
| 76 | 1.0 | 4/10[d] |
| 76 | 2.0 | 4/10[e] |
| 77 | 2.0 | 4/10[e] |

[a]Administered by gavage
[b]Compound number from Tables I-VIII
[c]Dose administered in 0.1-ml of solution equivalent to the presumed amount of compound which would be consumed by chicks drinking medicated water at the concentration indicated over a 24-hour period
[d]13/20 Infected non-medicated chicks died in this test
[e]11/20 Infected non-medicated chicks died in this test The compounds of this invention have also exhibited in vivo activity against experimental infections caused by Mycoplasma gallisepticum. In these tests infections were induced in chicks by injecting 0.2 ml of a broth culture of M. gallisepticum into the abdominal air sac of two- to three-day-old chicks. The compounds were administered by gavage five times at a dose equivalent to 0.5 g/gal (on the day of challenge once prior to and once following the challenge, two times on the next day and once on the third day). Twenty-one days post-infection, the chicks were weighed, a blood sample was taken, and the chicks were sacrificed. The presence or absence of air-sac lesions was recorded. The results of these tests are summarized in Table XIV.

TABLE XIV

Antimycoplasmal Activity of C-20-Modified Derivatives in Chicks

| Test Compound[a] | Mortality | Number with Air-Sac Lesions/ Number Treated | Number with Antibodies[b]/ Number Tested |
|---|---|---|---|
| 24 | 0/10 | 6/10 | 10/10 |
| 26 | 1/10 | 5/10 | 7/9 |
| 33 | 0/10 | 2/10 | 10/10 |

TABLE XIV-continued

Antimycoplasmal Activity of C-20-Modified Derivatives in Chicks

| Test Compound[a] | Mortality | Number with Air-Sac Lesions/ Number Treated | Number with Antibodies[b]/ Number Tested |
|---|---|---|---|
| 44 | 0/10 | 7/10 | 9/10 |
| 75 | 1/10 | 3/10 | 9/9 |
| Infected Control | 2/10 | 10/10 | 8/8 |
| Normal Control | 0/0 | 0/0 | 0/0 |

[a]Compound numbers from Tables I–VIII
[b]Antibodies to M. gallisepticum

This invention also relates to methods of controlling infections caused by bacterial and mycoplasmal species. In carrying out the methods of this invention, an effective amount of a compound of formulas 1–4 is administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 1 to about 100 mg/kg and preferably will be in the range of from about 1 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of infections caused by bacteria and Mycoplasma species. These compositions comprise a compound of formulas 1–4 together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a compound of formulas 1–4.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided. In these examples the abbreviations "20-DH" and "20-DH-DO" are used for the terms "20-dihydro" and "20-dihydro-20-deoxy", respectively.

PREPARATION 1

20-Dihydrotylosin (Relomycin)

A solution of tylosin base (30.0 g, 32.8 mmole) in 2-propanol (300 ml) and water (200 ml) was treated with sodium borohydride (315 mg, 8.2 mmole), portionwise, over five minutes. Thirty minutes after the addition was completed, the pH of the reaction solution was adjusted to 7.0 by the addition of a 1 N sulfuric acid solution. The neutralized solution was evaporated under vacuum to remove the 2-propanol; the aqueous solution remaining was treated with a saturated sodium bicarbonate solution (500 ml). The mixture was extracted with dichloromethane (3×300 ml), and the combined extract was washed with a saturated sodium chloride solution (1×200 ml) and dried over sodium sulfate. Filtration followed by evaporation gave a glass which was broken up in n-hexane, collected on a filter and air dried to yield 28.5 g (95%) of 20-dihydrotylosin.

PREPARATION 2

20-Dihydrodesmycosin

Desmycosin (10 g, 13 mmoles), dissolved in isopropanol:water (1:1, 175 ml), was stirred at room temperature while $NaBH_4$ (125 mg, 3.3 mmoles) was added. After ½ hour the pH of the reaction mixture was adjusted to 7.0 with 1 N $H_2SO_4$. The alcohol was removed under reduced pressure. Saturated $NaHCO_3$ solution was added to the aqueous solution, and the product was extracted into $CH_2Cl_2$. The organic layer was dried ($Na_2SO_4$), and solvent was removed under reduced pressure to give 9.65 g of 20-dihydrodesmycosin (12.5 mmoles, 96% yield) as a white foam.

PREPARATION 3

20-DH-DO-20-iododesmycosin (Method 1)

20-Dihydrodesmycosin (2.0 g, 2.6 mmoles) and tetra n-butylammonium iodide (1.5 g, 3.9 mmoles) were dissolved in $CH_2Cl_2$ (30 ml) with s-collidine (0.6 ml, 4.5 mmoles) added. This solution was cooled to $-78°$ C. under a nitrogen atmosphere and treated with trifluoromethanesulfonic anhydride (0.6 ml, 3.9 mmoles) dropwise by syringe. The reaction was stirred for 5 minutes at $-78°$ C. and then allowed to come to room temperature (about 30 minutes). Saturated $NaHCO_3$ solution was added, and the product was extracted with $CH_2Cl_2$. The organic layer was dried ($Na_2SO_4$) and evaporated to give a red oil which was purified by silica-gel flash chromatography, eluting initially with $CH_2Cl_2$ (400 ml) and then stepwise with $CH_2Cl_2:CH_3OH$ solutions as follows: 98:2 (250 ml); 96:4 (500 ml) 95:5 (250 ml); 94:6 (750 ml) and 92:8 (250 ml). Fractions containing the desired product were identified by TLC, combined and evaporated to dryness to give 20-DH-DO-20-iododesmycosin (595 mg, 0.67 mmoles, 26% yield) as a white foam.

PREPARATION 4

20-DH-DO-20-iododesmycosin (Method 2)

20-Dihydrodesmycosin (5.0 g, 6.5 mmoles) and triphenylphosphine (2.54 g, 9.70 mmoles) were dissolved in dimethylformamide (DMF) (10 ml). This mixture was stirred at room temperature under $N_2$ while iodine (2.46 g, 9.70 mmoles) in DMF (5 ml) was added dropwise. The reaction mixture was stirred for two hours and then poured into cold saturated $NaHCO_3$ solution. The product was extracted with $CHCl_3$ (two portions) and the combined $CHCl_3$ extracts were shaken with 0.1 M sodium thiosulfate to remove unreacted iodine. The organic layer was dried ($Na_2SO_4$) and evaporated under reduced pressure to give a light yellow oil which was purified by silica-gel flash chromatography. The column was eluted initially with $CH_2Cl_2$ (500 ml) and then with 250 ml portions of $CH_2Cl_2:CH_3OH$ mixtures as follows: 98:2; 96:4; 95:5; 94:6; 92:8; 88:12; and 86:14. Fractions containing the desired product were identified as in Preparation 2 and combined to give 1.78 g (2.0 mmoles, 31% yield) of 20-DH-DO-20-iododesmycosin as a white foam.

PREPARATION 5

20-DH-20-O-(p-Toluenesulfonyl)tylosin

A solution of 20-dihydrotylosin (10.0 g, 10.9 mmole) and 4-(N,N-dimethylamino)pyridine (24 mg, 0.2 mmole) in dichloromethane (100 ml) and pyridine (10 ml) was treated with p-toluenesulfonyl chloride (2.08 g, 10.9 mmole). The resulting solution was stirred at room temperature with the exclusion of moisture. Additional p-toluenesulfonyl chloride was added after three hours (1.0 g, 5.2 mmole) and after twenty-two hours (240 mg, 1.3 mmole). After twenty-seven hours, methanol (0.8 ml) was added, and the solution was evaporated to give a glass. The glass was dissolved in dichloromethane, washed with saturated sodium bicarbonate solution and dried over sodium sulfate. The solution was filtered and then evaporated to give a glass that was purified by silica-gel flash chromatography. Elution with a gradient of 1 L of dichloromethane to 1 L of methanol/dichloromethane (3.5:96.5) and then with 2 L of methanol/dichloromethane (3.5:96.5) gave 5.37 g (46%) of pure 20-DH-DO-20-O-(p-toluenesulfonyl)tylosin and 2.3 g (20%) of slightly impure 20-DH-20-O-(p-toluenesulfonyl)tylosin.

EXAMPLE 1

20-DH-DO-20-N-Phthalimidotylosin

A solution of 20-dihydrotylosin (3.0 g, 3.27 mmole), triphenylphosphine (1.714 g, 6.54 mmole) and phthalimide (962 mg, 6.54 mmole) in tetrahydrofuran (50 ml) under argon was treated dropwise, over one minute, with diethyl azodicarboxylate (1.03 ml, 6.54 mmole). Thirty minutes after the addition was completed, methanol (0.3 ml) was added; after ten minutes, the reaction was evaporated under vacuum to give a glass. This glass was purified by silica-gel flash chromatography, eluting with dichloromethane (300 ml) and then gradients of 1 L of dichloromethane to 1 L of methanol/dichloromethane (3:97) and 1 L of methanol/dichloromethane (3:97) to 1 L of methanol/dichloromethane (6:94), to give 2.35 g (70%) of 20-DH-DO-20-N-phthalimidotylosin.

EXAMPLE 2

20-DH-DO-20-N-Phthalimidodesmycosin

A solution of 20-DH-DO-20-N-phthalimidotylosin (1.04 g, 1.0 mmole) in 1 N sulfuric acid (50 ml) was stirred at room temperature for one hour. The reaction solution was carefully added to a saturated sodium bicarbonate solution (100 ml), and the resulting mixture was extracted with dichloromethane ($3 \times 30$ ml). The combined extract was dried over sodium sulfate. Filtration followed by evaporation yielded 890 mg (99%) of 20-DH-DO-20-N-phthalimidodesmycosin.

EXAMPLE 3

20-DH-DO-20-[(1-N-Methyltetrazol-5-yl)thio]tylosin

A solution of 20-dihydrotylosin (3.0 g, 3.27 mmole) and triphenylphosphine (1.714 g, 6.54 mmole) in tetrahydrofuran (50 ml) under argon was treated dropwise, over one minute, with diethyl azodicarboxylate (1.05 ml, 6.54 mmole). One minute after the addition was completed, 5-mercapto-1-N-methyltetrazole (760 mg, 6.54 mmole) was added in one portion. Thirty minutes later, methanol (1 ml) was added, and the reaction solution was evaporated. The residue obtained was dissolved in ethyl acetate and extracted three times with 0.1 M acetic acid solution. The acidic extracts were combined and saturated by the careful addition of solid sodium bicarbonate. The resulting mixture was extracted three times with dichloromethane. The extracts were combined and dried over sodium sulfate. The solution was filtered and then evaporated to give a glass. The glass was purified by silica-gel flash chromatography, eluting first with dichloromethane (300 ml) and then with a gradient of 1 L of dichloromethane to 1 L of methanol/dichloromethane (3:97) followed by one of 1 L of methanol/dichloromethane (3:97) to 1 L of methanol/dichloromethane (1:9), to give 2.24 g (67%) of 20-DH-DO-20-[(1-N-methyltetrazol-5-yl)thio]tylosin.

EXAMPLE 4

20-DH-DO-20-[(1-N-Methyltetrazol-5-yl)thio]desmycosin

20-DH-DO-20-[(1-N-Methyltetrazol-5-yl)thio]tylosin (1.2 g, 1.18 mmole) was treated, using a procedure like that of Example 2, to give 920 mg (89%) of 20-DH-DO-20-[(1-N-methyltetrazol-5-yl)thio]desmycosin.

EXAMPLE 5

20-DH-DO-20-Chlorotylosin

A solution of 20-dihydrotylosin (3.0 g, 3.27 mmole), triphenylphosphine (2.57 g, 9.8 mmole) and carbon tetrachloride (0.48 ml, 4.9 mmole) in dichloromethane (60 ml) and pyridine (6 ml) was stirred at room temperature, under argon, for sixty-four hours. The reaction was treated with methanol (1 ml) and stirred for thirty minutes before being evaporated to give a glass. The glass was dissolved in dichloromethane, diluted with an equal volume of cyclohexane and evaporated. This process was repeated several times. The resulting pyridine-free glass was purified by silica-gel flash chromatography, eluting with dichloromethane (300 ml) and then a gradient of 1 L of dichloromethane to 1 L of methanol/dichloromethane (7:93), to give 2.06 g (67%) of 20-DH-DO-20-chlorotylosin.

EXAMPLE 6

20-DH-DO-20-Chlorodesmycosin

20-Chlorotylosin (935 mg, 1.0 mmole) was treated, using a procedure like that of Example 2, to give 790 mg (100%) of 20-DH-DO-20-chlorodesmycosin.

EXAMPLE 7

20-DH-20-O-Phenyltylosin

Using a procedure like that described in Example 1, 20-dihydrotylosin (3.0 g, 3.27 mmole), triphenylphosphine (1.714 g, 6.54 mmole), phenol (615 mg, 6.54 mmole) and diethyl azodicarboxylate (1.05 ml, 6.54 mmole) were reacted to give a crude glass. The glass was purified by silica-gel chromatography on a Waters Prep 500, eluting first with 1 L of dichloromethane, then with a gradient of 2 L of dichloromethane to 2 L of methanol/dichloromethane (5:95) and finally with 2 L of methanol/dichloromethane (5:95), to give 2.07 g (64%) of 20-DH-20-O-phenyltylosin.

EXAMPLE 8

20-DH-20-O-Phenyldesmycosin

20-DH-20-O-Phenyltylosin (1.2 g, 1.2 mmole) was treated, using a procedure like that of Example 2, to give 1.02 g (100%) of 20-DH-20-O-phenyldesmycosin.

EXAMPLE 9

20-DH-20-O-(Phenoxyacetyl)tylosin

A solution of 20-dihydrotylosin (5.0 g, 5.45 mmole) in dichloromethane (50 ml) and pyridine (3 ml) at 0° C. was treated dropwise, over fifteen minutes, with a solution of phenoxyacetyl chloride (0.75 ml, 5.45 mmole) in dichloromethane (5 ml). Additional phenoxyacetyl chloride was added after forty-five minutes (0.25 ml, 1.82 mmole) and after sixty-five minutes (0.25 ml, 1.82 mmole). After two hours, methanol (1 ml) was added. The reaction was stirred for fifteen minutes, and then washed with a saturated sodium bicarbonate solution and dried over sodium sulfate. The solution was filtered and evaporated to give a glass. The glass was purified by silica-gel flash chromatography, eluting with dichloromethane (100 ml), a gradient of 1 L of dichloromethane to 1 L of methanol/dichloromethane (3.5:96.5) and then 1 L of methanol/dichloromethane (3.5:96.5) to give 3.4 g (59%) of 20-DH-20-O-(phenoxyacetyl)-tylosin.

EXAMPLE 10

20-DH-20-O-(Phenoxyacetyl)desmycosin

20-DH-20-O-(Phenoxyacetyl)tylosin (1.4 g, 1.3 mmole) was treated, using a procedure like that in Example 2, to give 1.0 g (83%) of 20-DH-20-O-(phenoxyacetyl)desmycosin.

EXAMPLE 11

20-DH-DO-20-Azidotylosin

A solution of 20-dihydrotylosin (9.17 g, 10.0 mmole) and triphenylphosphine (5.24 g, 20.0 mmole) in tetrahydrofuran (200 ml) under argon at 0° C. was treated dropwise, over one minute, with diethyl azodicarboxylate (3.3 ml, 20 mmole). Five minutes after the addition was complete, the reaction was treated with diphenylphosphoryl azide (4.31 ml, 20 mmole), dropwise, over five minutes. Ten minutes after this addition was complete, the cooling bath was removed; thirty-five minutes later, methanol (2 ml) was added. Thirty minutes later the reaction solution was evaporated. The residue obtained was dissolved in dichloromethane, washed with saturated sodium bicarbonate solution and dried over sodium sulfate. The solution was filtered and evaporated to give a glass. The glass was purified by silica-gel chromatography on a Waters Prep 500, eluting first with 2 L of dichloromethane and then with gradients of 4 L of dichloromethane to 4 L of methanol/dichloromethane (5:95) and 2 L of methanol/dichloromethane (5:95) to 2 L of methanol/dichloromethane (7.5:92.5), to give 5.23 g (56%) of 20-DH-DO-20-azidotylosin.

EXAMPLE 12

20-DH-DO-20-Azidodesmycosin

20-DH-DO-20-Azidotylosin (3.25 g, 3.45 mmole) was treated, using a procedure like that of Example 2, to give 2.75 g (100%) of 20-DH-DO-20-azidodesmycosin.

EXAMPLE 13

20-DH-DO-20-N-Phthalimido-2'-O-propionyltylosin

A solution of 20-DH-DO-20-N-phthalimidotylosin (600 mg, 0.57 mmole) in acetone (10 ml) was treated with propionic anhydride (0.15 ml, 1.15 mmole) and stirred at room temperature with the exclusion of moisture. After fifteen hours the reaction was treated with additional propionic anhydride (0.07 ml, 0.54 mmole). Twenty-four hours later, the reaction was poured into saturated sodium bicarbonate solution (50 ml). The resulting mixture was extracted three times with dichloromethane. The extracts were combined, dried over sodium sulfate, filtered, and evaporated to give a quantitative yield of 20-DH-DO-20-N-phthalimido-2'-O-propionyltylosin.

EXAMPLE 14

20-DH-DO-20-N-Phthalimido-2'-O-propionyldesmycosin

A solution of 20-DH-DO-20-N-phthalimido-2'-O-propionyltylosin (490 mg, 0.44 mmole) in 1 N sulfuric acid (10 ml) and dioxane (1 ml) was stirred at room temperature for one hour. The reaction mixture was carefully saturated with solid sodium bicarbonate and extracted three times with dichloromethane. The extracts were combined, dried over sodium sulfate, filtered, and evaporated to give a quantitative yield of 20-DH-DO-20-N-phthalimido-2'-O-propionyldesmycosin.

EXAMPLE 15

20-DH-DO-20-N-Phthalimido-2',4'-di-O-propionyldesmycosin

A solution of 20-DH-DO-20-N-phthalimido-2'-O-propionyldesmycosin (220 mg, 0.23 mmole) in acetone (8 ml) was treated with propionic anhydride (0.06 ml, 0.46 mmole) and stirred at room temperature with the exclusion of moisture for one week. The reaction was poured into saturated sodium bicarbonate solution (40 ml), and the resulting mixture was extracted three times with dichloromethane. The extracts were combined, dried over sodium sulfate, filtered and evaporated to give 220 mg (94%) of 20-DH-DO-20-N-phthalimido-2',4'-di-O-propionyldesmycosin.

EXAMPLE 16

20-DH-20-O-Phenyl-2'-O-acetyltylosin

A solution of 20-DH-20-O-phenyltylosin (5.0 g, 5.04 mmole) in acetone (90 ml) was treated with acetic anhydride (2.0 ml, 21.2 mmole) and stirred at room temperature with the exclusion of moisture for sixteen hours. The reaction mixture was evaporated to one-half volume and poured into a saturated sodium bicarbonate solution (200 ml). The resulting mixture was extracted three times with dichloromethane. The extracts were combined, dried over sodium sulfate, filtered and evaporated to give a quantitative yield of 20-DH-20-O-phenyl-2'-O-acetyltylosin.

EXAMPLE 17

20-DH-20-O-Phenyl-2'-O-acetyldesmycosin

20-DH-20-O-Phenyl-2'-O-acetyltylosin (4.5 g, 4.35 mmole) was treated, using a procedure like that in Example 2, to give a crude glass. The glass was purified by silica-gel flash chromatography, eluting with dichloromethane (300 ml) and then a gradient of 1 L of dichloromethane to 1 L of methanol/dichloromethane (5:95), to give 2.9 g (75%) of 20-DH-20-O-phenyl-2'-O-acetyldesmycosin.

EXAMPLE 18

20-DH-20-O-Phenyl-2',4'-di-O-acetyldesmycosin

A solution of 20-DH-20-O-phenyl-2'-O-acetyldesmycosin (610 mg, 0.69 mmole) in acetone (20 ml) was treated with acetic anhydride (0.40 ml, 4.03 mmole) and stirred at room temperature with the exclusion of moisture for forty hours. The reaction mixture was treated, using a procedure like that described in Example 15, to give 625 mg (98%) of 20-DH-20-O-phenyl-2',4'-di-O-acetyldesmycosin.

EXAMPLE 19

20-DH-DO-20-Chloro-2'-O-propionyltylosin

A solution of 20-DH-DO-20-chlorotylosin (770 mg, 0.82 mmole) in acetone (20 ml) was treated with propionic anhydride (0.3 ml, 2.5 mmole) and stirred at room temperature with the exclusion of moisture for three days. A work-up like that in Example 15 gave a glass. The glass was purified by silica-gel flash chromatography, eluting with a gradient of 500 ml of dichloromethane to 500 ml of methanol/dichloromethane (4:96), to give 380 mg (47%) of 20-DH-DO-20-chloro-2'-O-propionyltylosin.

EXAMPLE 20

20-DH-DO-20-Chloro-2'-O-propionyldesmycosin

A solution of 20-DH-DO-20-chloro-2'-O-propionyltylosin (250 mg, 0.25 mmole) in 1 N sulfuric acid (25 ml) was stirred for one hour at room temperature. A work-up like that in Example 17 gave 209 mg (98%) of 20-DH-DO-20-chloro-2'-O-propionyldesmycosin.

EXAMPLE 21

Deformyl-19-(1,3-Dioxolan-2-yl)desmycosin

A solution of desmycosin (3.0 g, 3.89 mmole) in acetonitrile (20 ml) and ethylene glycol (15 ml) was treated with powdered 4 A molecular sieves and p-toluenesulfonic acid monohydrate (1.11 g., 5.84 mmole) and stirred at room temperature with the exclusion of moisture for one hour. The reaction mixture was neutralized by the addition of solid sodium bicarbonate (600 mg) and filtered. The filtrate was poured into a saturated sodium bicarbonate solution. The resulting solution was extracted three times with dichloromethane. The extracts were combined, washed with saturated sodium chloride solution and then with water, dried over sodium sulfate, filtered and evaporated to give a glass. The glass was purified by silica-gel flash chromatography, eluting with a gradient of 1 L of dichloromethane to 1 L of methanol/dichloromethane (1:9) and then with 500 ml of methanol/dichloromethane (1:9) to give 1.46 g (46%) of deformyl-19-(1,3-dioxolan-2-yl)desmycosin.

EXAMPLE 22

20-DH-DO-20-Aminotylosin

A solution of 20-DH-DO-20-azidotylosin (728 mg, 0.77 mg) and triphenylphosphine (213 mg, 0.81 mmole) in tetrahydrofuran (25 ml) and water (0.1 ml) was stirred at room temperature for a week. Triphenylphosphine (150 mg, 0.57 mmole) and water (0.1 ml) were added to the reaction, which was then stirred for five days. The reaction mixture was evaporated to give a glass. The glass was dissolved in ethyl acetate and extracted three times with 0.1 M acetic acid. The aqueous extracts were combined, carefully saturated with solid sodium bicarbonate and then extracted three times with dichloromethane. The extracts were combined, dried over sodium sulfate, filtered and evaporated to give a glass. The glass was purified by preparative silica-gel TLC, using a dichloromethane/methanol/concentrated ammonium hydroxide (90:10:2) solvent, to give 200 mg (28%) of 20-DH-DO-20-aminotylosin.

EXAMPLE 23

20-DH-DO-20-[N-(Phenylacetyl)amino]tylosin

In a procedure like that described in Example 22, 20-DH-DO-20-azidotylosin (975 mg, 1.04 mmole) and triphenylphosphine (465 mg, 1.77 mmole) were reacted in tetrahydrofuran (40 ml) and water (0.4 ml) for thirteen days. After the addition of water (2 ml) and N-phenylacetoxysuccinimide (253 mg, 1.09 mmole), the reaction mixture was stirred for two hours at room temperature. The reaction mixture was evaporated and worked up as in Example 22 to yield a glass. The glass was purified by silica-gel flash chromatography, eluting with dichloromethane (300 ml) and then with a gradient of 1 L of dichloromethane to 1 L of methanol/dichloromethane (9:91) to give 170 mg (16%) of 20-DH-DO-20-[N-(phenylacetyl)amino]tylosin and 77 mg (8%) of 20-DH-DO-20-azidotylosin.

EXAMPLE 24

20-DH-20-O-Cinoxacinyltylosin

A solution of 20-dihydrotylosin (3.0 g, 3.27 mmole) in dichloromethane (50 ml) and pyridine (0.8 ml) under argon at 0° C. was treated with cinnoxacinyl chloride (1.175 g, 4.2 mmole, added in four portions). One hour after the last addition, the reaction mixture was washed with a saturated sodium bicarbonate solution, dried over sodium sulfate, filtered and evaporated. The powder obtained was purified by silica-gel flash chromatography, eluting with a gradient of 1 L of dichloromethane to 1 L of methanol/dichloromethane (1:4) to give 1.4 g (37%) of pure 20-DH-20-O-cinoxacinyltylosin and 1.68 g (44%) of slightly impure product.

EXAMPLE 25

20-DH-20-O-Cinoxacinyldesmycosin

20-DH-20-O-Cinoxacinyltylosin (1.68 g, 1.45 mmole) was treated with 1 N sulfuric acid, using a procedure like that of Example 2, to give a glass. The glass was purified by silica-gel flash chromatography, eluting with a gradient of 1 L of dichloromethane to 1 L of methanol/dichloromethane (17:83) to yield 1.1 g (75%) of 20-DH-20-O-cinnoxacinyldesmycosin.

EXAMPLE 26

20-DH-20-O-Methyldesmycosin and 20-DH-20-O-NO$_2$-desmycosin

Silver nitrate (875 mg, 5.3 mmol) was added to a solution of 20-DH-DO-20-iododesmycosin (1.8 g, 2 mmol) in methanol (90 ml) at room temperature, and the mixture was stirred for five hours. The reaction mixture was filtered and evaporated to dryness under reduced pressure. The resulting solid was redissolved in dichloromethane and extracted with sodium bicarbonate solution. The organic layer was dried over sodium sulfate, filtered and evaporated to dryness to give a crude product. This product was separated by flash chromatography on silica gel (Grace 60) eluting with a gradient of 1 L of EtOAc to 1 L of EtOAc/MeOH/NH$_4$OH (94:4:2) to give 690 mg of partially purified products along with 180 mg of crude 23-O-mycinosyl-20-dihydro-5,20-O-cycloanhydrotylonolide. The 690 mg (supra) was chromatographed as before, eluting with a gradient of 1 L of ethyl acetate to 1 L of EtOAc/MeOH/NH$_4$OH (85:10:5) to give 128 mg of 20-DH-20-O-NO$_2$-desmycosin, 205 mg of 20-DH-20-O-methyldesmycosin and 20 mg of 20-dihydrodesmycosin.

EXAMPLE 27

20-DH-20-O-(Phenethyl)desmycosin

Silver nitrate (348 mg, 2.0 mmol) was added to a solution of 20-DH-DO-20-iododesmycosin (780 mg, 0.9 mmol) in phenethyl alcohol (35 ml), and the mixture was stirred at room temperature for 20 hours. The reaction mixture was filtered and evaporated to give an oil which was purified by silica-gel flash chromatography, eluting with a gradient of 1 L of CH$_2$Cl$_2$ to 1 L of CH$_2$Cl$_2$:MeOH (85:15) to give 30 mg of 20-DH-20-O-(phenethyl)desmycosin along with 105 mg of 23-O-mycinosyl-20-dihydro-5,20-O-cycloanhydrotylonolide.

EXAMPLE 28

20-DH-DO-20-[N-(Ethoxycarbonyl)-N-(ethoxycarbonylamino)]aminotylosin

A solution of 20-dihydrotylosin (3.0 g, 3.27 mmole) and triphenylphosphine (1.286 g, 4.91 mmole) in dichloromethane (50 ml) under argon was treated with diethylazodicarboxylate (0.81 ml, 4.91 mmole) all at once. After the reaction mixture was stirred for thirty minutes, additional triphenylphosphine (429 mg, 1.64 mmole) and diethylazodicarboxylate (0.27 ml, 1.64 mmole) were added. One hour later, methanol (1 ml) was added, and the reaction mixture was evaporated to give a glass. The glass was purified by silica-gel flash chromatography, eluting with a gradient of 1 L of dichloromethane to 1 L of methanol/dichloromethane (4:96) and then with 1 L of methanol/dichloromethane (4:96), to give 2.0 g (57% yield) of 20-DH-DO-20-[N-(ethoxycarbonyl)-N-(ethoxycarbonylamino)-]aminotylosin.

EXAMPLE 29

20-DH-DO-20-[N-(Ethoxycarbonyl)-N-(ethoxycarbonylamino)]aminodesmycosin

This compound was prepared from 20-DH-DO-20-[N-ethoxycarbonyl)-N-(ethoxycarbonylamino)-]aminotylosin as described in Example 2.

EXAMPLE 30

20-DH-DO-20-Fluoro-tylosin

A solution of 20-DH-DO-20-O-(P-toluenesulfonyl)-tylosin (2.125 g, 1.98 mmole) in tetrahydrofuran (75 ml) under argon was treated with tetrabutylammonium fluoride dihydrate (460 mg, 2.5 mmole) and heated at reflux. After one hour additional tetrabutylammonium fluoride dihydrate (100 mg, 0.54 mmole) was added, and refluxing was continued for three hours. The cooled reaction mixture was filtered and evaporated to a glass. The glass was dissolved in dichloromethane, washed with saturated sodium bicarbonate solution, dried over sodium sulfate, filtered and evaporated to give a glass. The glass was purified by silica-gel flash chromatography, eluting with a gradient of 1 L of dichloromethane to 1 L of methanol/dichloromethane (1:9) to give 1.52 g (83% yield) of 20-DH-DO-20-fluorotylosin.

EXAMPLE 31

20-DH-DO-20-Fluorodesmycosin

This compound was prepared from 20-DH-DO-20-fluorotylosin as described in Example 2.

EXAMPLE 32

20-Deformylmacrocin

A mixture of macrocin (1.80 g, 2.0 mmole) and Wilkinson's catalyst in acetonitrile (60 ml) under argon was refluxed 1.75 hours. The reaction mixture was evaporated, treated with ethyl acetate and filtered. The filtrate was extracted with 0.1 M acetic acid solution, and the combined acid extract was brought to pH=8.5 by the addition of 1 N sodium hydroxide solution. The resulting mixture was extracted with dichloromethane, and the combined extract was dried over sodium sulfate, filtered and evaporated to give a glass. The glass was purified by silica-gel flash chromatography, eluting with dichloromethane/methanol/concentrated ammonium hydroxide (18:1:0.1) to give 450 mg (26% yield) of 20-deformylmacrocin.

EXAMPLE 33

Deformyl-19-(Benzothiazolidin-2-yl)desmycosin

A solution of desmycosin (2.0 g, 2.6 mmole) in dichloromethane (40 ml) was treated with 2-aminothiophenol (400 mg, 2.9 mmole) and stirred at room temperature with the exclusion of moisture for twenty minutes. The reaction was washed with saturated sodium bicarbonate solution, dried over sodium sulfate, filtered and evaporated to give a glass. The glass was purified by silica-gel flash chromatography, eluting with a gradient of 1 L of dichloromethane to 1 L of methanol/dichloromethane (1:9) to give 1.8 g (79% yield) of deformyl-19-(benzothiazolidin-2-yl)desmycosin.

EXAMPLE 34

20-DH-20-(p-Formylphenyl)desmycosin

A solution of 20-DH-desmycosin (15.4 g, 19.9 mmole), triphenylphosphine (10.44 g, 39.8 mmole) and p-hydroxybenzaldehyde (4.86 g, 39.8 mmole) in tetrahydrofuran (300 ml) under argon was treated with diethylazodicarboxylate (6.3 ml, 39.8 mmole) all at once. After 1.3 hours, methanol (15 ml) was added, and the reaction mixture was evaporated. The resulting glass was purified by silica-gel chromatography on a Waters Prep 500, eluting first with 2 L of dichloromethane, then with a gradient of 4 L of dichloromethane to 4 L of methanol/dichloromethane (1:7) and finally with 2 L of methanol/dichloromethane (1:7) to give 10.19 g (58% yield) of 20-DH-20-O-(p-formylphenyl)desmycosin.

EXAMPLE 35

20-DH-20-O-Phenyl-2',4'-di-O-acetyl-4",3-di-O-(tetrahydropyran-2-yl)desmycosin A solution of 20-DH-20-O-phenyl-2',4'-di-O-acetyldesmycosin (3.53 mmole) in dichloromethane (50 ml) was treated with distilled dihydropyran (3.4 ml, 37.2 mmole) and pyridinium p-toluenesulfonate (1.33 g, 5.3 mmole) and refluxed under argon overnight. The reaction mixture was washed with sodium chloride solution and then with sodium bicarbonate solution, dried over sodium sulfate, filtered, and evaporated to give a quantitative yield of 20-DH-20-O-phenyl-2',4'-di-O-acetyl-4",3-di-O-(tetrahydropyran-2-yl)desmycosin as a mixture of diastereomers.

EXAMPLE 36

20-DH-20-O-Phenyl-4",3-di-O-(tetrahydropyran-2-yl)desmycosin

A solution of 20-DH-20-O-phenyl-2',4'-di-O-acetyl-4",3-di-O-(tetrahydropyran-2-yl)desmycosin (3.53 mmole) in methanol (50 ml) was heated at 50° C. under argon overnight. The reaction mixture was evaporated to give a quantative yield of 20-DH-20-O-phenyl-4",3-di-O-(tetrahydropyran-2-yl)desmycosin as a mixture of diastereomers.

EXAMPLE 37

20-DH-20-O-Phenyl-4",3-di-O-THP-4'-iododesmycosin

A solution of 20-DH-20-O-phenyl-4",3-di-O-(tetrahydropyran-2-yl)desmycosin (660 mg, 0.65 mmole) in pyridine was cooled to $-35°$ C. under argon and treated with benzylsulfonyl chloride (191 mg, 1.0 mmole). After one hour, water (0.024 ml) was added; five minutes later, the cold reaction mixture was evaporated to a small volume, taken up in toluene and evaporated to 20% of the original volume. This mixture was treated with a saturated sodium bicarbonate solution. The organic layer was separated, dried over sodium sulfate, filtered and evaporated, finally from toluene (2 times) to give an oil (avoid extended evaporation). This oil was dissolved in methyl ethyl ketone (20 ml), treated with sodium iodide (250 mg, 1.67 mmole) and refluxed under argon twenty-five minutes. The cooled mixture was evporated, dissolved in toluene, and filtered. The filtrate was washed with (1) a mixture of saturated sodium bicarbonate solution (20 ml) and 0.1 M sodium thiosulfate solution (10 ml), (2) water, and (3) saturated sodium bicarbonate solution and then was dried over sodium sulfate, filtered and evaporated. The crude product thus obtained was purified by silica-gel flash chromatography, eluting with a gradient of 0.5 L toluene to 0.5 L ethyl acetate to give 470 mg (64% yield) of 20-DH-20-O-phenyl-4",3-di-O-THP-4'-iododesmycosin as a mixture of diastereomers.

EXAMPLE 38

20-DH-20-O-Phenyl-2'-O-acetyl-4'-deoxydesmycosin

A solution of 20-DH-20-O-phenyl-4",3-di-O-(tetrahydropyran-2-yl)-4'-iodo-desmycosin (460 mg, 0.41 mmole) in benzene (15 ml) was treated with tri-n-butyltin hydride (0.11 ml, 0.41 mmole) and a catalytic amount of 2,2'-azobis(2-methylpropionitrile) (AIBN) and refluxed under argon for one hour. The reaction mixture was evaporated to an oil and treated with 1 N sulfuric acid solution (20 ml), n-hexane (10 ml) and tetrahydrofuran (30 ml). The resulting mixture was stirred for two hours and then was evaporated to aqueous and saturated by the addition of solid sodium bicarbonate. This solution was extracted with dichloromethane, and the combined extract was dried over sodium sulfate, filtered and evaporated to give an oil which was dissolved in acetonitrile and extracted with n-hexane (2 times). The acetonitrile solution was evaporated to a glass. To facilitate chromatographic purification, this glass was dissolved in acetone and treated with acetic anhydride (0.2 ml, 2.12 mmole) for 1.5 hours. The reaction mixture was worked up as in Example 15 to give a glass (370 mg) which was purified by silica-gel flash chromatography. Elution with 0.6 L of dichloromethane to 0.6 L of methanol/dichloromethane (1:9) gave 155 mg (43% yield) of 20-DH-20-O-phenyl-2'-O-acetyl-4'-deoxydesmycosin.

EXAMPLE 39

20-DH-20-O-Phenyl-4'-deoxydesmycosin

A solution of 20-DH-20-O-phenyl-2'-O-acetyl-4'-deoxydesmycosin (130 mg, 0.15 mmole) in methanol was heated at 55° C. for 3.25 hours. The reaction mixture was evaporated to give a quantitative yield of 20-DH-20-O-phenyl-4'-deoxydesmycosin.

EXAMPLE 40

20-DH-20-O-[p-(Hexahydroazepin-1-ylmethyl)phenyl]desmycosin

A solution of 20-DH-20-O-(p-formylphenyl)desmycosin (2.43 g, 2.78 mmole) and hexamethyleneimine (0.94 ml, 8.33 mmole) in methanol (25 ml) under argon was treated with 3 A molecular sieves (3 g). After thirty minutes sodium cyanoborohydride (623 mg, 9.9 mmole) was added, and the stirring was continued for 2.5 hours. The reaction mixture was poured into sodium bicarbonate solution, and the resulting solution was extracted with ethyl acetate. The ethyl acetate extract was washed with saturated sodium chloride solution, dried over sodium sulfate, filtered, and evaporated to give a glass. The glass was purified by silica-gel flash chromatography, eluting with a gradient of 1 L of dichloromethane to 1 L of methanol/dichloromethane (1:4) to give 1.71 g (64% yield) of 20-DH-20-O-[p-(hexahydroazepin-1-ylmethyl)phenyl]desmycosin.

EXAMPLE 41

20-DH-DO-20-Aminodesmycosin diacetate

A solution of 20-DH-DO-20-azidodesmycosin (2.0 g, 2.51 mmole) and triphenylphosphine (690 mg, 2.65 mmole) in tetrahydrofuran (40 ml) under argon was refluxed for fifteen hours; water (0.2 ml) was then added; and refluxing was continued for four hours. The reaction mixture was evaporated to a glass, treated with 0.1 M acetic acid solution (75 ml) and stirred vigorously for two hours. The resulting mixture was filtered, and the filtrate was lyophilized. The resulting glass was dissolved in a mininum amount of water and filtered, and the filtrate was lyophilized to give 2.0 g (89% yield) of 20-DH-DO-20-aminodesmycosin diacetate.

EXAMPLE 42

20-DH-DO-20-(N-phenoxyacetyl)aminodesmycosin (Alternate Method)

A solution of 20-DH-DO-20-aminodesmycosin diacetate (1.44 g, 1.6 mmole) in acetone (25 ml) and water (10 ml) was treated with potassium carbonate (234 mg, 1.70 mmole) and then with N-(phenoxyacetyloxy)succinimide (425 mg, 1.7 mmole). After one hour, methanol (1 ml) was added, and ten minutes later, the reaction mixture was evaporated to aqueous, treated with saturated sodium bicarbonate solution (25 ml) and extracted with dichloromethane. The combined extract was dried over sodium sulfate, filtered, and evaporated to give a glass. The glass was purified by silica-gel flash chromatography, eluting with a gradient of 1 L of dichloromethane to 1 L of methanol/dichloromethane (1:9) to give 885 mg (61% yield) of 20-DH-DO-20-(N-phenoxyacetyl)aminodesmycosin.

EXAMPLE 43

20-DH-DO-20-(p-Toluenesulfonyl)desmycosin

A solution of 20-iododesmycosin (5.0 g, 5.66 mmole) and tetrabutylammonium p-toluenesulfinate (2.7 g, 6.8 mmole) in tetrahydrofuran (100 ml) under argon was refluxed for 2.5 hours. The reaction mixture was evaporated to a glass which was purified by silica-gel chromatography on a Waters Prep 500. Elution with a gradient of 4 L of dichloromethane to 4 L of methanol/dichloromethane (18:82) yielded 4.7 g of impure product. Further purification by silica-gel flash chromoatography, eluting with a gradient of 1 L of dichloromethane to 1 L of methanol/dichloromethane (7:93) and then with 1.5 L of methanol/dichloromethane (7:93) gave 1.35 g (26% yield) of pure and 2.18 g (42%) of slightly impure 20-DH-DO-20-(p-toluenesulfonyl)desmycosin.

EXAMPLES 44–53

20-DH-DO-20-(Phenylthio)tylosin was prepared, using a procedure like that of Example 3, and 20-DH-DO-20-(phenylthio)desmycosin was prepared using a procedure like that of Example 4.

The following tylosin derivatives were prepared using a procedure like that of Example 7:

20-DH-20-O-(p-Nitrophenyl)tylosin
20-DH-20-O-(p-Benzoylphenyl)tylosin
20-DH-20-O-(p-Methoxyphenyl)tylosin
20-DH-20-O-(3,5-Dichlorophenyl)tylosin
20-DH-20-O-[m-(N,N-Dimethylamino)phenyl]tylosin
20-DH-20-O-(p-Formylphenyl)tylosin
20-DH-20-O-(p-Phenylphenyl)tylosin
20-DH-20-O-(Pyridin-3-yl)tylosin

EXAMPLE 54

20-DH-20-O-[2,2,2-Trifluoro-1-(trifluormethyl)ethyl]tylosin was prepared using the method of Example 3.

EXAMPLES 55–74

The following derivatives were prepared by procedures analogous to those of the preceding preparations and examples:

20-DH-20-O-(Phenylsulfinyl)desmycosin
20-DH-20-O-Acetyldesmycosin
20-DH-20-O-[2,2,2-trifluoro-1-(trifluoromethyl)ethyl]desmycosin
20-DH-20-O-(p-Nitrophenyl)desmycosin
20-DH-20-O-(p-Methoxyphenyl)desmycosin
20-DH-20-O-(p-Benzoylphenyl)desmycosin
20-DH-20-O-[p-(Ethoxycarbonyl)phenyl]desmycosin
20-DH-20-O-[m-(N,N-Dimethylamino)phenyl]desmycosin
20-DH-20-O-(3,5-Dichlorophenyl)desmycosin
20-DH-20-O-(p-Phenylphenyl)desmycosin
20-DH-20-O-(p-Phenoxyphenyl)desmycosin
20-DH-20-O-(m-Phenoxyphenyl)desmycosin
20-DH-20-O-(Pyridin-3-yl)desmycosin
20-DH-20-O-(5,6-Diphenyl-1,2,4-triazin-3-yl)desmycosin
20-DH-20-O-(Quinazolin-4-yl)desmycosin
20-DH-DO-20-Iodomacrocin
20-DH-20-O-Phenylmacrocin
20-DH-20-O-(p-Toluenesulfonyl)macrocin
20-DH-DO-20-Iodolactenocin 20-DH-20-O-Phenyllactenocin

EXAMPLE 75

20-DH-DO-Lactenocin can be prepared by reducing 20-DH-DO-20-iodolactenocin with tri-n-butyltin hydride in toluene, using a catalytic amount of AIBN, at about 80° C. under argon for about two hours.

EXAMPLES 76–79

The following compounds can be prepared from the corresponding 2'-O-acyl compounds, using a procedure like that of Example 15:

20-DH-DO-20-N-Phthalimido-2',4'-di-O-acetyldesmycosin,
20-DH-20-O-Phenyl-2',4'-di-O-propionyldesmycosin,
20-DH-20-O-(p-Nitrophenyl)-2',4'-di-O-propionyldesmycosin, and
20-DH-20-O-phenyl-2'-O-acetyl-4'-O-propionyldesmycosin.

EXAMPLES 80–102

The following derivatives can be prepared by procedures analogous to those of the preceding examples:
20-DH-DO-macrocin
20-Deformyllactenocin
20-DH-DO-20-[(1-Methyltetrazol-5-yl)thio]DOMM
20-DH-DO-20-[(1-Methyltetrazol-5-yl)thio]DOML
20-DH-DO-20-(Chloro)macrocin
20-DH-DO-20-(Chloro)lactenocin
20-DH-DO-20-(Fluoro)DOMM
20-DH-DO-20-(Fluoro)DOML
20-DH-DO-20-(Phenylthio)macrocin
20-DH-DO-20-(Phenylthio)lactenocin
20-DH-20-O-(p-Nitrophenyl)macrocin
20-DH-20-O-(p-Nitrophenyl)lactenocin
20-DH-20-O-(p-Methoxyphenyl)DOMM
20-DH-20-O-(p-Methoxyphenyl)DOML
20-DH-20-O-(Phenyl)DOMM
20-DH-20-O-(Phenyl)DOML
20-DH-DO-20-(Azido)macrocin
20-DH-DO-20-(Azido)lactenocin
20-DH-DO-20-N-Phthalimido-DOMM
20-DH-DO-20-N-Phthalimido-DOML
20-DH-20-O-(p-Toluenesulfonyl)lactenocin
20-DH-DO-20-(N-phenoxyacetyl-amino)lactenocin
20-DH-DO-20-(N-phenoxyacetyl-amino)-4'-deoxydesmycosin Tables XV–XVIII which follow summarize certain physical data on illustrative compounds of this invention.

TABLE XV

Physical Characteristics of C-20-Modified Derivatives of Tylosin

| 20-Substituent | Compound[a] No. | FDMS Parent Ion | UV $\lambda$max $(\epsilon)$[b] | NMR[c] $\delta$ | IR[d] cm$^{-1}$ | TLC[e] $R_f$ |
|---|---|---|---|---|---|---|
| phthalimido group (structure shown) | 1 | 1047 (m$^+$ + 1) | 220 (42,500) 282 (21,500) | 7.94 (broad s, 2H) 7.76 (broad s, 2H) | | |
| —N$_3$ | 2 | 943 (m$^+$ + 1) | 282 (25,300) | | 2096 | |
| —NH—AcPh | 3 | 1035 (m$^+$ + 1) | 284 (21,500) | 5.68 (broad s, 1H) 7.24–7.50 (m, 6H) | | |
| —OPh | 4 | 993 (m$^+$) | 278 (25,000) 220 (13,500) | 6.84–7.0 (m, 2H) 7.20–7.40 (m, 4H) | | |
| —S—(1-methyltetrazol-5-yl) (structure shown) | 5 | 1016 (m$^+$ + 1) | 282 (22,000) | 3.98 (s) | | |
| —SPh | 6 | 1010 (m$^+$ + 1) | 204 (14,500) 258 shoulder (17,500) 281 (23,500) | 7.06–7.50 (m, 6H) | | |
| —Cl | 7 | 935 (m$^+$) | 282 (23,300) | | | 0.52 |
| —F | 8 | 920 (m$^+$ + 1) | 282 (23,000) | 4.16–4.64 [2 doublets (s1 and s3) overlapping multiplet, 4H] | | |
| HN—CO$_2$Et / —N—CO$_2$Et | 9 | 1076 (m$^+$ + 1) | 286 (21,750) | 8.06 (s, 1H) | | 0.57 |
| —O—cinoxacinyl | 10 | 1162 (m$^+$ + 1) | 220 (19,500) 250 (28,750) 270 (30,500) 351 (13,500) 365 shoulder (12,750) | | | 0.54 |
| —OOC—CH$_2$OPh | 11 | 1052 (m$^+$ + 1) | 280 (22,500) | 4.68 (d, 2H) 6.9–7.08 (m, 2H) 7.2–7.4 (m, 4H) | | |
| —O—(p-NO$_2$Ph) | 12 | 1039 (m$^+$ + 1) | 225 (11,400) | 6.94 (d, 2H) | | |

TABLE XV-continued

Physical Characteristics of C-20-Modified Derivatives of Tylosin

| 20-Substituent | Compound[a] No. | FDMS Parent Ion | UV λmax (ε)[b] | NMR[c] δ | IR[d] cm$^{-1}$ | TLC[e] R$_f$ |
|---|---|---|---|---|---|---|
| —O—(p-BzPh) | 13 | 1098 (m$^+$ + 1) | 287 (30,350)<br>225 shoulder (13,500)<br>285 (37,000) | 8.00 (d, 2H)<br>6.8–7.0 (d, 2H)<br>7.26–7.62 (m, 4H)<br>7.66–7.90 (m, 4H) | | |
| —O—(p-MeOPh) | 14 | 1024 (m$^+$ + 1) | 225 (11,920)<br>284 (22,500) | 3.74 (s, 3H) | | |
| —O—(3,5-diClPh) | 15 | 1062 (m$^+$) | 203 (48,000)<br>207 (46,500)<br>224 shoulder (12,100)<br>228 shoulder (22,100)<br>283 (22,200) | 6.8 (s, 2H)<br>6.92 (s, 1H) | | |
| —O—[m-(NMe$_2$)Ph] | 16 | 1037 (m$^+$ + 1) | 212 (28,750)<br>260 shoulder (18,000)<br>283 (24,300) | 2.94 (s, 6H) | | |
| —O—(p-CHOPh) | 17 | 1022 (m$^+$ + 1) | 220 (16,500)<br>282 (41,500) | 9.88 (s, 1H)<br>6.98 (d, 2H)<br>7.80 (d, 2H) | | |
| —O—(p-PhPh) | 18 | 1069 (m$^+$) | 271 (31,200) | 9.6 (d, 2H) | | |
| —OCH(CF$_3$)$_2$ | 19 | 1068 (m$^+$ + 1) | 282 (21,300) | | | 0.56 |

[a] Compound numbers from Table I
[b] In ethanol
[c] 360 or 270 MHz, run in CDCl$_3$ (TMS)
[d] Run in CHCl$_3$
[e] Silica gel adsorbent; solvent system-CH$_2$Cl$_2$:MeOH:NH$_4$OH (90:10:2)

TABLE XVI

Physical Characteristics of C-20-Modified Derivatives of Desmycosin

| 20-Substituent | Compound[a] No. | FDMS Parent Ion | UV λmax (ε)[b] | NMR[c] δ | IR[d] cm$^{-1}$ | TLC[e] R$_f$ |
|---|---|---|---|---|---|---|
| —Cl | 21 | 791 (m$^+$) | 282 (22,700) | | | 0.43 |
| —F | 22 | 775 (m$^+$) | 282 (22,500) | 4.24–4.70 (2d over m, 4H) | | |
| —SPh | 23 | 865 (m$^+$) | 203 (15,700)<br>260 shoulder (17,800)<br>281 (23,300) | 7.1–7.44 (m, 6H) | | |
| —S—C(=N-N=N-N(CH$_3$)) (1-methyltetrazol-5-ylthio) | 24 | 872 (m$^+$ + 1) | 282 (22,000) | 3.98 (s, 3H) | | |
| —OS(=O)Ph | 25 | 912 (m$^+$ + 1) | 223 (10,700)<br>248 shoulder (9,000)<br>282 (20,000) | | | |
| —OOC—CH$_2$OPh | 26 | 908 (m$^+$ + 1) | 218 shoulder (9,000)<br>282 (22,000) | 4.68 (d, 2H)<br>6.9–7.1 (m, 2H)<br>7.2–7.4 (m, 4H) | | |
| —O—cinoxacinyl | 27 | 1018 (m$^+$ + 1) | 222 (15,700)<br>252 (25,000)<br>275 (29,300)<br>358 (11,500)<br>365 shoulder (10,600) | | | 0.43 |
| —O—NO$_2$ | 28 | 819 (m$^+$ + 1) | 282 (21,800) | | | |
| —OAc | 29 | 815 (m$^+$) | 282 (22,100) | 2.09 (s, 3H) | | |
| —OMe | 30 | 787 (m$^+$) | 282 (19,200) | 3.30 (s, 3H) | | |
| —O—(CH$_2$)$_2$Ph | 31 | 877 (m$^+$) | 282 (17,600) | | | |
| —OCH(CF$_3$)$_2$ | 32 | 924 (m$^+$ + 1) | 282 (20,500) | | | |
| —OPh | 33 | 849 (m$^+$) | 220 (14,000)<br>278 (26,000) | 6.84–7.0 (m, 2H)<br>7.18–7.40 (m, 4H) | | |
| —O—(p-NO$_2$Ph) | 34 | 895 (m$^+$ + 1) | 227 (8,400)<br>285 (27,400) | 6.94 (d, 2H)<br>8.0 (d, 2H) | | |
| —O—(p-MeOPh) | 35 | 879 (m$^+$) | 225 (12,750)<br>283 (22,900) | 3.80 (s, 3H) | | |
| —O—(p-CHOPh) | 36 | 877 (m$^+$) | 220 (14,300)<br>284 (38,500) | 9.88 (s, 1H)<br>6.99 (d, 2H)<br>7.83 (d, 2H) | | |

TABLE XVI-continued
Physical Characteristics of C-20-Modified Derivatives of Desmycosin

| 20-Substituent | Compound[a] No. | FDMS Parent Ion | UV λmax (ε)[b] | NMR[c] δ | IR[d] cm$^{-1}$ | TLC[e] $R_f$ |
|---|---|---|---|---|---|---|
| —O—(p-BzPh) | 37 | 954 (m$^+$ + 1) | 225 shoulder (12,300)<br>285 (34,500) | 6.95 (d, 2H)<br>7.70–7.94 (m, 4H)<br>7.42–7.66 (m, 3H) | | |
| —O—(p-EtCO$_2$Ph) | 38 | 922 (m$^+$ + 1) | 207 shoulder (16,200)<br>265 (28,300) | 6.90 (d, 2H)<br>7.98 (d, 2H) | | |
| —O—[m-(NMe$_2$)Ph] | 39 | 892 (m$^+$) | 210 (27,600)<br>257 shoulder (16,200)<br>282 (22,500) | 2.90 (s, 6H) | | |
| —O—(3,5-diClPh) | 40 | 917,919 (m$^+$) | 222 shoulder (9,800)<br>282 (21,000) | 6.80 (s, 2H)<br>6.94 (s, 1H) | | |
| —O—(p-PhPh) | 41 | 925 (m$^+$) | 272 (33,800) | 6.9–7.04 (d, 2H) | | |
| —O—[p-[(CH$_2$)$_6$N—CH$_2$—]Ph] | 42 | 961 (m$^+$ + 1) | 226 (14,200)<br>281 (22,200) | 6.83 (d, 2H)<br>7.14–7.40 (d, 2H over d, 4H) | | |
| 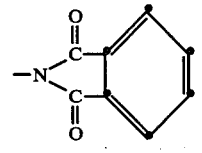 | 43 | 903 (m$^+$ + 1) | 219 (41,700)<br>241 (12,500)<br>282 (21,000) | 7.78 (broad s, 2H)<br>7.95 (broad s, 2H) | | |
| —N$_3$ | 44 | 798 (m$^+$) | 282 (24,000) | | 2097 | |
| 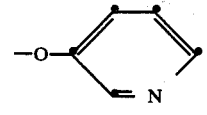 | 45 | 931 (m$^+$) | 286 (22,000) | 8.05 (s, 1H) | | |
| —SO$_2$(p-MePh) | 46 | 912 (m$^+$ + 1) | 224 (13,700)<br>282 (22,500) | 2.46 (s, 3H)<br>7.38 (d, 2H)<br>7.83 (d, 2H) | | |
| —O—[p-(PhO)Ph] | 47 | 942 (m$^+$ + 1) | 227 (17,700)<br>281 (22,800) | 6.8–7.1 (m, 6H)<br>7.2–7.4 (m, 4H) | | |
| —O—[m-(PhO)Ph] | 48 | 942 (m$^+$ + 1) | 220 shoulder (22,500)<br>281 (22,300) | 6.5–6.7 (m, 2H)<br>7.0–7.4 (m, 8H) | | |
| 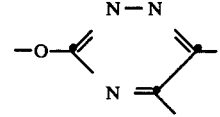 | 49 | 851 (m$^+$ + 1) | 218 (34,200)<br>278 (30,000) | 8.20 (t, 1H)<br>8.30 (s, 1H) | | |
|  | 50 | 1005 (m$^+$ + 1) | 278 (25,500) | 7.1–7.8 (m, 10H) | | |
| —O—(quinazolin-4-yl) | 51 | 902 (m$^+$ + 1) | 217 (25,340)<br>222 shoulder (25,000)<br>277 (24,000) | | | 0.52 |

[a] Compound numbers from Table II
[b] In ethanol
[c] 360 or 270 NHz, run in CDCl$_3$ (TMS)
[d] Run in CHCl$_3$
[e] Silica gel adsorbent; solvent system-CH$_2$Cl$_2$:MeOH:NH$_4$OH (90:10:2)

TABLE XVII
Physical Characteristics of C-20-Modified Derivatives of Macrocin

| 20-Substituent | Compound[a] No. | FDMS Parent Ion | UV λmax (ε)[b] | NMR[c] δ | IR[d] cm$^{-1}$ | TLC[e] $R_f$ |
|---|---|---|---|---|---|---|
| iodo | 52 | 1014 (m$^+$ + 1) | 280 (20,000) | | | 0.63 |
| —OPh | 53 | 980 (m$^+$ + 1) | 220 (18,750)<br>280 (33,500) | 6.9 (t, 3H)<br>7.25 (m, 7H) | | |
| deformyl | 54 | 874 (m$^+$ + 1) | 282 (22,700)[f] | 0.96–1.15 (2 overlapping doublets, 2 × 3H) | | |

TABLE XVII-continued

Physical Characteristics of C-20-Modified Derivatives of Macrocin

| 20-Substituent | Compound[a] No. | FDMS Parent Ion | UV λmax (ε)[b] | NMR[c] δ | IR[d] cm$^{-1}$ | TLC[e] R$_f$ |
|---|---|---|---|---|---|---|
| —O—(p-toluenesulfonyl) | 56 | 1058 (m$^+$ + 1) | | | 1180, 1350 | 0.54 |

[a]Compound numbers from Table III
[b]In methanol unless otherwise indicated
[c]360 or 270 MHz, run in CDCl$_3$ (TMS)
[d]Run in CHCl$_3$
[e]Silica-gel adsorbent; solvent system-CH$_2$Cl$_2$:MeOH:NH$_4$OH (90:10:0.5)
[f]Run in ethanol

TABLE XVIII

Physical Characteristics of C-20-Modified Derivatives of Lactenocin

| 20-Substituent | Compound[a] No. | FDMS Parent Ion | UV λmax (ε)[b] | NMR[c] δ | TLC[d] R$_f$ |
|---|---|---|---|---|---|
| iodo | 57 | 869 (m$^+$ + 1) | 280 (20,000) | 3.3-gain of 2H 9.7-loss of 20H | |
| —OPh | 58 | 836 (m$^+$ + 1) | 220 (18,500) 280 (23,000) | | 0.50 |
| H | 60 | 744 (m$^+$ + 1) | | 0.85 (t, 20H) | 0.45 |

[a]Compound numbers from Table IV
[b]In methanol
[c]360 or 270 MHz, run in CDCl$_3$ (TMS)
[d]Silica-gel adsorbent; solvent system-CH$_2$Cl$_2$:MeOH;NH$_4$OH (90:10:0.5)

EXAMPLE 103

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 base tartrate.

(E) A suspension is prepared by adding a finely ground formula 1 compound to carboxymethyl cellulose with thorough mixing so that the suspension contains 200 mg of the formula 1 base per ml of suspension.

EXAMPLE 104

Chick Ration for Control of Mycoplasma

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and B$_{12}$, choline, niacin, pantothenic acid, riboflavin, biotin, with glucose bulking agent) | 0.5 | 10 |
| Trace mineral premix (representing MnSO$_4$, ZnO, KI, FeSO$_4$, CaCO$_3$) | 0.2 | 4 |
| 2-Amino-4-hydroxybutyric acid (hydroxy analog of methionine) | 0.1 | 2 |
| Formula I compound | 0.01 | 0.2 |

These substances are mixed in accordance with standard feed-mixing techniques. Chicks fed such a ration, with water ad libitum, are protected against exposure to Mycoplasma infections.

We claim:

1. A compound of the formula

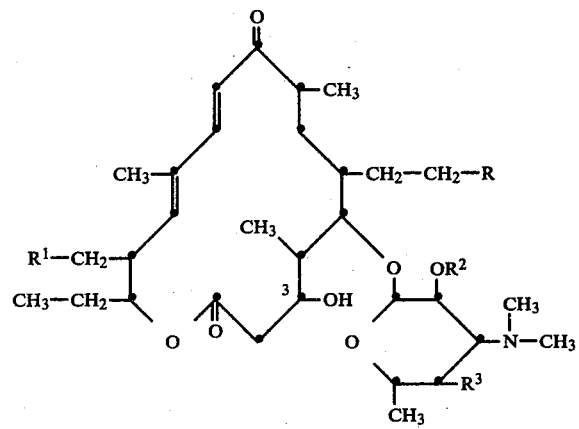

wherein
R is chloro, fluoro, —OR$^4$, —SR$^5$, —SO$_2$R$^6$, azido, —NHR$^7$, —N—phthalimido,

—N—NH—COOR$^8$ or —CN;

$R^1$ is

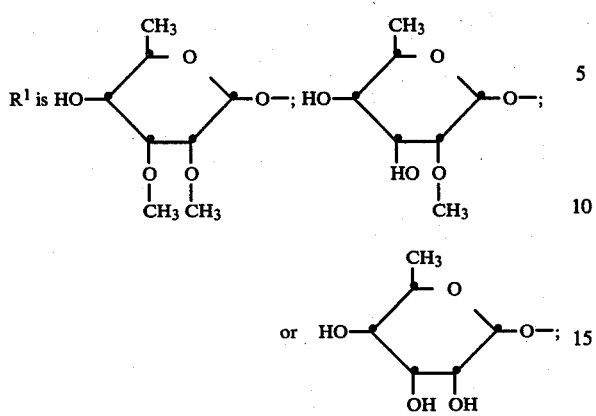

$R^2$ is hydrogen; $C_1$-$C_5$-alkanoyl; $C_1$-$C_5$-alkanoyl having from one to three halo substituents; benzoyl, phenylacetyl or phenylpropionyl; or benzoyl, phenylacetyl or phenylpropionyl having on the phenyl ring from one to five halo or methyl groups or from one to two methoxyl, nitro or hydroxyl groups;

$R^3$ is hydroxy; $C_1$-$C_5$-alkanoyloxy; $C_1$-$C_5$-alkanoyloxy having from one to three halo substituents; benzoyloxy, phenylacetoxy or phenoxyacetoxy; benzoyloxy, phenylacetoxy or phenoxyacetoxy having on the phenyl ring from one to five halo or methyl groups or from one to two methoxyl, nitro or hydroxyl groups; or

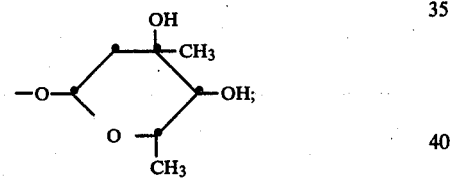

$R^4$ is $C_1$-$C_4$-alkyl; $C_1$-$C_4$-alkyl having one or more fluoro or chloro substituents; cyclohexyl; benzyl, phenethyl or phenoxyethyl; benzyl, phenethyl or phenoxyethyl having on the phenyl ring from one to five halo or methyl groups or from one to two methoxyl, nitro or hydroxyl groups; phenyl; derivatized phenyl; naphthyl; a heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; a selected heteroaryl group having at least one substituent selected from $C_1$-$C_4$-alkyl, halo, methoxy, ethoxy, hydroxy, oxo or phenyl; $C_1$-$C_5$-alkanoyl; $C_1$-$C_5$-alkanoyl having from one to three halo substituents; benzoyl, phenylacetyl, phenylpropionyl, phenoxyacetyl or phenylthioacetyl; benzoyl, phenylacetyl, phenylpropionyl, phenoxyacetyl or phenylthioacetyl having on the phenyl ring from one to five halo or methyl groups or from one to two methoxyl, nitro or hydroxyl groups; methanesulfonyl; trifluoromethanesulfonyl; phenylsulfinyl or phenylsulfonyl; phenylsulfinyl or phenylsulfonyl having on the phenyl ring from one to five halo or from one to two nitro groups; cinoxacinyl or —$NO_2$;

$R^5$ is $C_1$-$C_4$-alkyl; $C_1$-$C_4$-alkyl having one or more fluoro or chloro substituents; cyclohexyl; phenyl, benzyl or phenethyl; phenyl, benzyl or phenethyl having on the phenyl ring from one to five halo or methyl groups or from one to two methoxyl, nitro or hydroxyl groups; a heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; or a selected heteroaryl group having at least one substituent selected from $C_1$-$C_4$-alkyl, halo, methoxy, ethoxy, hydroxy, oxo or phenyl;

$R^6$ is $C_1$-$C_4$-alkyl; $C_1$-$C_4$-alkyl having one or more fluoro or chloro substituents; phenyl; or phenyl having from one to five halo or methyl or from one to two methoxyl, nitro or hydroxyl substituents;

$R^7$ is hydrogen; $C_1$-$C_5$-alkanoyl; $C_1$-$C_5$ alkanoyl having from one to three halo substituents; benzoyl, phenylacetyl, phenylpropionyl, phenoxyacetyl or phenylthioacetyl; benzoyl, phenylacetyl, phenylpropionyl, phenoxyacetyl, or phenylthioacetyl having on the phenyl ring from one to five halo or methyl groups or from one to two methoxyl, nitro or hydroxyl groups; or alkoxycarbonyl;

$R^8$ is methyl or ethyl; and halo is chloro, bromo or fluoro;

provided that, when $R^7$ is hydrogen, $R^2$ must be hydrogen and $R^3$ must be hydroxy; and that, when $R^1$ is

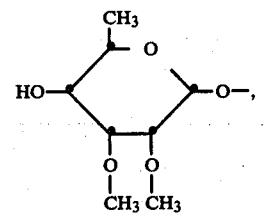

R cannot be chloro or fluoro; and its acid addition salts.

2. A compound of claim 1 wherein R is chloro.

3. The compound of claim 2 which is 20-dihydrodeoxy-20-chlorotylosin.

4. The compound of claim 2 which is 20-dihydrodeoxy-20-chlorodesmycosin.

5. A compound of claim 1 wherein R is fluoro.

6. The compound of claim 5 which is 20-dihydrodeoxy-20-fluorotylosin.

7. The compound of claim 5 which is 20-dihydrodeoxy-20-fluorodesmycosin.

8. A compound of claim 1 wherein R is —$OR^4$.

9. A compound of claim 8 wherein $R^4$ is phenyl.

10. The compound of claim 9 which is 20-dihydro-20-O-phenyldesmycosin.

11. The compound of claim 9 which is 20-dihydro-20-O-phenyltylosin.

12. The compound of claim 9 which is 20-dihydro-20-O-phenylmacrocin.

13. The compound of claim 9 which is 20-dihydro-20-O-phenyllactenocin.

14. A compound of claim 8 wherein $R^4$ is derivatized phenyl.

15. A compound of claim 14 wherein $R^4$ is p-nitrophenyl.

16. The compound of claim 15 which is 20-dihydro-20-O-(p-nitrophenyl)desmycosin.

17. A compound of claim 14 wherein $R^4$ is p-methoxyphenyl.

18. The compound of claim 17 which is 20-dihydro-20-O-(p-methoxyphenyl)desmycosin.

19. A compound of claim 14 wherein $R^4$ is p-formylphenyl.

20. The compound of claim 19 which is 20-dihydro-20-O-(p-formylphenyl)desmycosin.

21. A compound of claim 14 wherein $R^4$ is p-benzoylphenyl.

22. The compound of claim 21 which is 20-dihydro-20-O-(p-benzoylphenyl)desmycosin.

23. A compound of claim 14 wherein $R^4$ is m-(N,N-dimethylamino)phenyl.

24. The compound of claim 23 which is 20-dihydro-20-O-[m-(N,N-dimethylamino)phenyl]desmycosin.

25. A compound of claim 14 wherein $R^4$ is p-phenylphenyl.

26. The compound of claim 25 which is 20-dihydro-20-O-(p-phenylphenyl)desmycosin.

27. A compound of claim 14 wherein $R^4$ is (p-ethoxycarbonyl)phenyl.

28. The compound of claim 27 which is 20-dihydro-20-O-[(p-ethoxycarbonyl)phenyl]desmycosin.

29. A compound of claim 14 wherein $R^4$ is 3,5-dichlorophenyl.

30. The compound of claim 29 which is 20-dihydro-20-O-(3,5-dichlorophenyl)desmycosin.

31. A compound of claim 14 wherein $R^4$ is phenoxyphenyl.

32. The compound of claim 31 which is 20-dihydro-20-O-[(p-phenoxy)phenyl]desmycosin.

33. The compound of claim 31 which is 20-dihydro-20-O-[(m-phenoxy)phenyl]desmycosin.

34. A compound of claim 14 wherein $R^4$ is p-(hexahydroazepin-1-ylmethyl)phenyl.

35. The compound of claim 34 which is 20-dihydro-20-O-[p-(hexahydroazepin-1-ylmethyl)phenyl]desmycosin.

36. A compound of claim 14 wherein $R^4$ is (hydroxymethyl)phenyl.

37. The compound of claim 36 which is 20-dihydro-20-O-[p-(hydroxymethyl)phenyl]desmycosin.

38. A compound of claim 8 wherein $R^4$ is $C_1$-$C_4$-alkyl or $C_1$-$C_4$-alkyl having one or more fluoro or chloro substituents.

39. The compound of claim 38 which is 20-dihydro-20-O-[2,2,2-trifluoro-1-(trifluoromethyl)ethyl]desmycosin.

40. The compound of claim 38 which is 20-dihydro-20-O-methyldesmycosin.

41. A compound of claim 8 wherein $R^4$ is benzyl, phenethyl or phenoxyethyl or benzyl, phenethyl or phenoxyethyl having on the phenyl ring from one to five halo or methyl groups or from one to two methoxyl, nitro or hydroxyl groups.

42. The compound of claim 41 which is 20-dihydro-20-O-(phenethyl)desmycosin.

43. A compound of claim 8 wherein $R^4$ is a heteroaryl group or a heteroaryl group having at least one substituent selected from $C_1$-$C_4$-alkyl, halo, methoxy, ethoxy, hydroxy, oxo or phenyl.

44. A compound of claim 43 wherein $R^4$ is pyridinyl.

45. The compound of claim 44 which is 20-dihydro-20-O-(pyridin-3-yl)desmycosin.

46. A compound of claim 43 wherein $R^4$ is triazinyl.

47. The compound of claim 46 which is 20-dihydro-20-O-(5,6-diphenyl-1,2,4-triazin-3-yl)desmycosin.

48. A compound of claim 43 wherein $R^4$ is quinazolinyl.

49. The compound of claim 48 which is 20-dihydro-20-O-(quinazolin-4-yl)desmycosin.

50. A compound of claim 8 wherein $R^4$ is $C_1$-$C_5$-alkanoyl.

51. The compound of claim 50 which is 20-dihydro-20-O-acetyldesmycosin.

52. A compound of claim 8 wherein $R^4$ is benzoyl, phenylacetyl, phenylpropionyl, phenoxyacetyl or phenylthioacetyl or benzoyl, phenylacetyl, phenylpropionyl, phenoxyacetyl, or phenylthioacetyl having on the phenyl ring from one to five halo or methyl groups or from one to two methoxyl, nitro or hydroxyl groups.

53. The compound of claim 52 which is 20-dihydro-20-O-(phenoxyacetyl)desmycosin.

54. A compound of claim 8 wherein $R^4$ is methanesulfonyl or trifluoromethanesulfonyl.

55. The compound of claim 54 which is 20-dihydro-20-O-(trifluoromethanesulfonyl)desmycosin.

56. A compound of claim 8 wherein $R^4$ is phenylsulfinyl or phenylsulfonyl or phenylsulfinyl or phenylsulfonyl having on the phenyl ring from one to five halo or from one to two nitro groups.

57. The compound of claim 56 which is 20-dihydro-20-O-(phenylsulfinyl)desmycosin.

58. A compound of claim 8 wherein $R^4$ is cinoxacinyl.

59. The compound of claim 58 which is 20-dihydro-20-O-(cinoxacin-1-yl)desmycosin.

60. A compound of claim 8 wherein $R^4$ is —$NO_2$.

61. The compound of claim 60 which is 20-dihydro-20-O-nitrodesmycosin.

62. A compound of claim 1 wherein R is —$SR^5$.

63. A compound of claim 62 wherein $R^5$ is phenyl, benzyl or phenethyl or phenyl, benzyl or phenethyl having on the phenyl ring from one to five halo or methyl groups or from one to two methoxyl, nitro or hydroxyl groups.

64. A compound of claim 63 wherein $R^5$ is phenyl.

65. The compound of claim 64 which is 20-dihydro-20-deoxy-20-(phenylthio)desmycosin.

66. A compound of claim 63 wherein $R^5$ is phenyl having from one to five halo or methyl or from one to two methoxyl, nitro or hydroxyl substituents.

67. A compound of claim 62 wherein $R^5$ is a heteroaryl group or a heteroaryl group having at least one substituent selected from $C_1$-$C_4$-alkyl, halo, methoxy, ethoxy, hydroxy, oxo or phenyl.

68. A compound of claim 67 wherein $R^5$ is tetrazolyl.

69. The compound of claim 68 which is 20-dihydro-20-deoxy-20-[(1-methyltetrazol-5-yl)thio]desmycosin.

70. A compound of claim 1 wherein R is —$SO_2R^6$.

71. A compound of claim 70 wherein $R^6$ is phenyl or phenyl having from one to five halo or methyl or from one to two methoxyl, nitro or hydroxyl substituents.

72. The compound of claim 71 which is 20-dihydro-20-deoxy-20-(p-toluenesulfonyl)desmycosin.

73. A compound of claim 1 wherein R is azido.

74. The compound of claim 73 which is 20-dihydro-20-deoxy-20-azidodesmycosin.

75. A compound of claim 1 wherein R is —$NHR^7$.

76. A compound of claim 75 wherein $R^7$ is hydrogen.

77. The compound of claim 76 which is 20-dihydro-20-deoxy-20-aminodesmycosin.

78. A compound of claim 75 wherein $R^7$ is benzoyl, phenylacetyl, phenylpropionyl, phenoxyacetyl or phenylthioacetyl or benzoyl, phenylacetyl, phenylpropionyl, phenoxyacetyl or phenylthioacetyl having on the phenyl ring from one to five halo or methyl groups or from one to two methoxyl, nitro or hydroxyl groups.

79. The compound of claim 78 which is 20-dihydro-20-deoxy-20-[N-(phenoxyacetyl)amino]desmycosin.

80. A compound of claim 1 wherein R is —N—phthalimido.

81. The compound of claim 80 which is 20-dihydro-20-deoxy-20-N-phthalimidodesmycosin.

82. A compound of claim 1 wherein R is $$-\underset{|}{N}-NH-COOR^8$$
$$\phantom{-N-}COOR^8$$

83. The compound of claim 82 which is 20-dihydro-20-deoxy-20-[N-(ethoxycarbonyl-N-(ethoxycarbonylamino)]aminodesmycosin.

84. A compound of claim 1 wherein $R^2$ is $C_1$-$C_5$-alkanoyl or $C_1$-$C_5$-alkanoyl having from 1 to 3 halo substituents.

85. A compound of claim 84 wherein $R^2$ is acetyl.

86. The compound of claim 85 which is 20-dihydro-20-O-phenyl-2′-O-acetyldesmycosin.

87. The compound of claim 85 which is 20-dihydro-20-O-phenyl-2′,4′-di-O-acetyldesmycosin.

88. A compound of claim 84 wherein $R^2$ is propionyl.

89. The compound of claim 88 which is 20-dihydro-20-deoxy-20-N-phthalimido-2′-O-propionyldesmycosin.

90. The compound of claim 88 which is 20-dihydro-20-deoxy-20-N-phthalimido-2′,4′-di-O-propionyldesmycosin.

91. The compound of claim 88 which is 20-dihydro-20-deoxy-20-chloro-2′-O-propionyldesmycosin.

92. A compound of the formula wherein

Z is hydrogen, methyl, —CH$_2$Br, —CH$_2$I or —CH$_2$O(p-toluenesulfonyl);

$R^1$ is $R^2$ is hydrogen; $C_1$-$C_5$-alkanoyl; $C_1$-$C_5$-alkanoyl having from one to three halo substituents; benzoyl, phenylacetyl or phenylpropionyl; or benzoyl, phenylacetyl or phenylpropionyl having on the phenyl ring from one to five halo or methyl groups or from one to two methoxyl, nitro or hydroxyl groups;

$R^3$ is hydroxy; $C_1$-$C_5$-alkanoyloxy; $C_1$-$C_4$-alkanoyloxy having from one to three halo substituents; benzoyloxy, phenylacetoxy or phenoxyacetoxy; benzoyloxy, phenylacetoxy or phenoxyacetoxy having on the phenyl ring from one to five halo or methyl groups or from one to two methoxyl, nitro or hydroxyl groups; or and halo is chloro, bromo, or fluoro; and its acid addition salts.

93. A compound of claim 92 wherein Z is hydrogen.

94. The compound of claim 93 which is 20-deformylmacrocin.

95. The compound of claim 93 which is 20-deformyllactenocin.

96. A compound of claim 92 wherein Z is methyl.

97. The compound of claim 96 which is 20-dihydro-20-deoxymacrocin.

98. The compound of claim 96 which is 20-dihydro-20-deoxylactenocin.

99. A compound of claim 92 wherein Z is —CH$_2$I.

100. The compound of claim 99 which is 20-dihydro-20-deoxy-20-iodomacrocin.

101. The compound of claim 99 which is 20-dihydro-20-deoxy-20-iodolactenocin.

102. A compound of claim 92 wherein Z is —CH$_2$O(p-toluenesulfonyl).

103. A compound of claim 92 wherein $R^2$ is $C_1$-$C_5$-alkanoyl or $C_1$-$C_5$-alkanoyl having from one to three halo substituents.

104. A compound of claim 103 wherein $R^2$ is acetyl.

105. A compound of claim 103 wherein $R^2$ is propionyl.

106. A compound of the formula

51

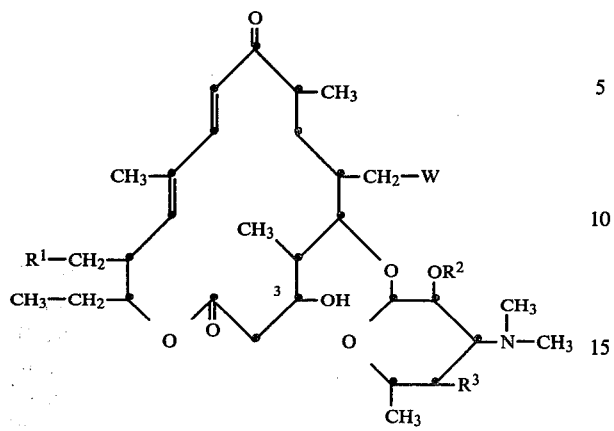

wherein
W represents

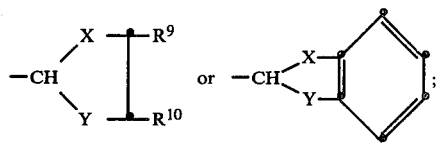

X and Y, independently, represent O, S, NH, N—CH₃, N-phenyl or N-benzyl;

$R^9$ and $R^{10}$, independently, are hydrogen, methyl, phenyl, methoxycarbonyl, ethoxycarbonyl or phenoxycarbonyl;

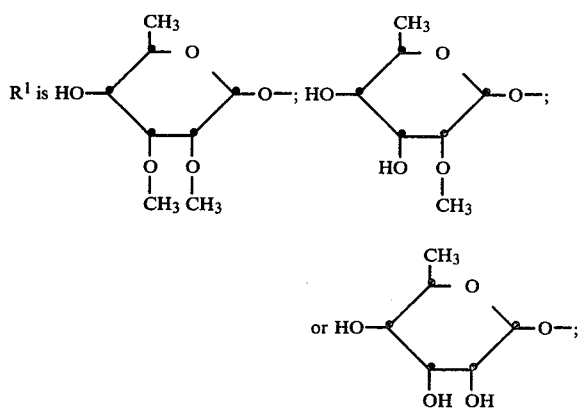

$R^2$ is hydrogen; $C_1$-$C_5$-alkanoyl; $C_1$-$C_5$-alkanoyl having from one to three halo substituents; benzoyl, phenylacetyl or phenylpropionyl; or benzoyl, phenylacetyl or phenylpropionyl having on the phenyl ring from one to five halo or methyl groups or from one to two methoxyl, nitro or hydroxyl groups;

$R^3$ is hydroxy; $C_1$-$C_5$-alkanoyloxy; $C_1$-$C_5$-alkanoyloxy having from one to three halo substituents; benzoyloxy, phenylacetoxy or phenoxyacetoxy; benzoyloxy, phenylacetoxy or phenoxyacetoxy having on the phenyl ring from one to five halo or methyl groups or from one to two methoxyl, nitro or hydroxyl groups; or

52

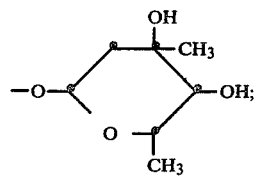

and halo is chloro, bromo or fluoro; and its acid addition salts.

107. A compound of claim 106 wherein W is

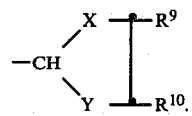

108. A compound of claim 107 wherein X and Y are oxygen and $R^9$ and $R^{10}$ are hydrogen.

109. The compound of claim 108 wherein $R^1$ is

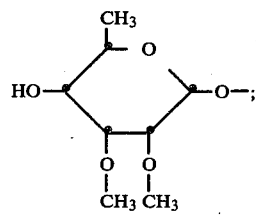

$R^2$ is hydrogen, and $R^3$ is hydroxy.

110. A compound of claim 107 wherein X is S, Y is NH, $R^9$ is hydrogen and $R^{10}$ is ethoxycarbonyl.

111. The compound of claim 110 wherein $R^1$ is

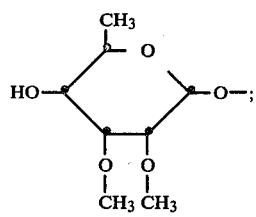

$R^2$ is hydrogen and $R^3$ is hydroxy.

112. A compound of claim 107 wherein X is S, Y is N-benzyl, and $R^9$ and $R^{10}$ are hydrogen.

113. The compound of claim 112 wherein $R^1$ is

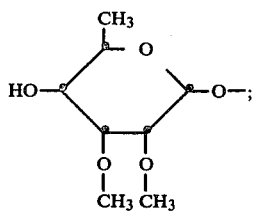

$R^2$ is hydrogen and $R^3$ is hydroxy.

114. A compound of claim 106 wherein W is

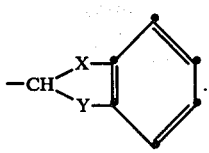

115. A compound of claim 114 wherein X is S and Y is NH.

116. The compound of claim 115 wherein $R^1$ is

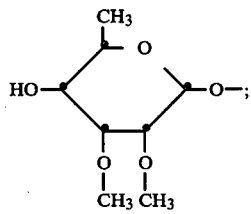

$R^2$ is hydrogen and $R^3$ is hydroxy.

117. A compound of claim 106 wherein $R^2$ is $C_1$–$C_5$-alkanoyl or $C_1$–$C_5$-alkanoyl having from 1 to 3 halo substituents.

118. A compound of claim 117 wherein $R^2$ is acetyl.

119. A compound of claim 117 wherein $R^2$ is propionyl.

120. A compound of the formula

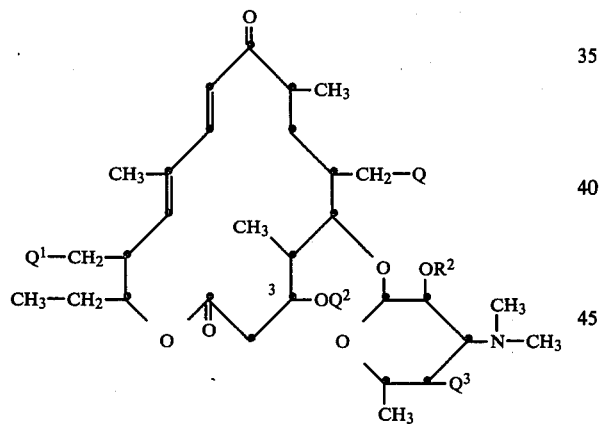

wherein
Q is —$CH_2R$ or W;
$Q^1$ is

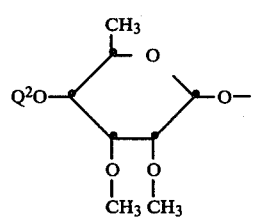

$Q^2$ is hydrogen or a hydroxyl-protecting group;
$Q^3$ is hydrogen or iodo;
R is chloro, fluoro, —$OR^4$, —$SR^5$, —$SO_2R^6$, azido, —$NHR^7$, —N—phthalimido,

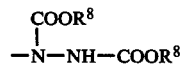

or —CN;

$R^2$ is hydrogen; $C_1$–$C_5$-alkanoyl; $C_1$–$C_5$-alkanoyl having from one to three halo substituents; benzoyl, phenylacetyl or phenylpropionyl; or benzoyl, phenylacetyl or phenylpropionyl having on the phenyl ring from one to five halo or methyl groups or from one to two methoxyl, nitro or hydroxyl groups;

$R^4$ is $C_1$–$C_4$-alkyl; $C_1$–$C_4$-alkyl having one or more fluoro or chloro substituents; cyclohexyl; benzyl, phenethyl or phenoxyethyl; benzyl, phenethyl or phenoxyethyl having on the phenyl ring from one to five halo or methyl groups or from one to two methoxyl, nitro or hydroxyl groups; phenyl; derivatized phenyl; naphthyl; a heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; a specified heteroaryl group having at least one substituent selected from $C_1$–$C_4$-alkyl, halo, methoxy, ethoxy, hydroxy, oxo or phenyl; $C_1$–$C_5$-alkanoyl; $C_1$–$C_5$-alkanoyl having from one to three halo substituents; benzoyl, phenylacetyl, phenylpriopionyl, phenoxyacetyl or phenylthioacetyl; benzoyl, phenylacetyl, phenylpropionyl, phenoxyacetyl or phenylthioacetyl having on the phenyl ring from one to five halo or methyl groups or from one to two methoxyl, nitro or hydroxyl groups; methanesulfonyl; trifluoromethanesulfonyl; phenylsulfinyl or phenylsulfonyl; phenylsulfinyl or phenylsulfonyl having on the phenyl ring from one to five halo or from one to two nitro groups; cinoxacinyl; or —$NO_2$;

$R^5$ is $C_1$–$C_4$-alkyl; $C_1$–$C_4$-alkyl having one or more fluoro or chloro substituents; cyclohexyl; phenyl, benzyl or phenethyl; phenyl, benzyl or phenethyl having on the phenyl ring from one to five halo or methyl groups or from one to two methoxyl, nitro or hydroxyl groups; a heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; or a specified heteroaryl group having at least one substituent selected from $C_1$–$C_4$-alkyl, halo, methoxy, ethoxy, hydroxy, oxo or phenyl;

$R^6$ is $C_1$–$C_4$-alkyl; $C_1$–$C_4$-alkyl having one or more fluoro or chloro substituents; phenyl or phenyl having from one to five halo or methyl or from one to two methoxyl, nitro or hydroxyl substituents;

$R^7$ is hydrogen; $C_1$–$C_5$-alkanoyl; $C_1$–$C_5$-alkanoyl having from one to three halo substituents; benzoyl, phenylacetyl, phenylpropionyl, phenoxyacetyl or phenylthioacetyl; benzoyl, phenylacetyl, phenylpropionyl, phenoxyacetyl or phenylthioacetyl having on the phenyl ring from one to five halo or methyl groups or from one to two methoxyl, nitro or hydroxyl groups; or alkoxycarbonyl;

$R^8$ is methyl or ethyl;

$R^9$ and $R^{10}$, independently, are hydrogen, methyl, phenyl, methoxycarbonyl, ethoxycarbonyl or phenoxycarbonyl;

W represents

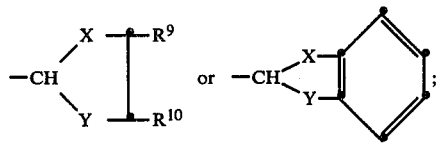

X and Y, independently, represent O, S, NH, N—CH$_3$, N-phenyl or N-benzyl; and halo is chloro, bromo or fluoro;

provided that the Q$^2$ substituents must be identical and that R$^2$ must be hydrogen when R$^7$ is hydrogen; and its acid addition salts.

121. A compound of claim 120 wherein Q$^3$ is hydrogen.

122. A compound of claim 120 wherein Q is phenoxymethyl.

123. The compound of claim 122 which is 20-dihydro-20-O-phenyl-2'-O-acetyl-4'-deoxydesmycosin.

124. The compound of claim 122 which is 20-dihydro-20-O-phenyl-4'-deoxydesmycosin.

125. A compound of claim 120 wherein R is derivatized phenyl.

126. A compound of claim 120 wherein R$^2$ is C$_1$–C$_5$-alkanoyl or C$_1$–C$_5$-alkanoyl having from from one to three halo substituents.

127. A compound of claim 126 wherein R$^2$ is acetyl or propionyl.

128. A composition useful for the treatment of susceptible bacterial or mycoplasmal infections comprising a compound of claim 1 wherein the acid addition salt is a pharmaceutically acceptable one and a suitable vehicle.

129. A composition useful for treatment of susceptible bacterial or mycoplasmal infections comprising a compound of claim 92 wherein the acid addition salt is a pharmaceutically acceptable one and a suitable vehicle.

130. A composition useful for the treatment of susceptible bacterial or mycoplasmal infections comprising a compound of claim 106 wherein the acid addition salt is a pharmaceutically acceptable one and a suitable vehicle.

131. A composition useful for the treatment of susceptible bacterial or mycoplasmal infections comprising a compound of claim 120 wherein the acid addition salt is a pharmaceutically acceptable one and a suitable vehicle.

132. A method for treating infections caused by Mycoplasma species which comprises administering an amount of a composition of claim 128 which is effective against the Mycoplasma species to an infected or susceptible warm-blooded animal.

133. A method for treating infections caused by Mycoplasma species which comprises administering an amount of a composition of claim 129 which is effective against the Mycoplasma species to an infected or susceptible warm-blooded animal.

134. A method for treating infections caused by Mycoplasma species which comprises administering an amount of a composition of claim 130 which is effective against the Mycoplasma species to an infected or suspectible warm-blooded animal.

135. A method for treating infections caused by Mycoplasma species which comprises administering an amount of a composition of claim 131 which is effective against the Mycoplasma species to an infected or susceptible warm-blooded animal.

136. A method for treating infections caused by susceptible gram-positive bacteria which comprises administering to an infected or susceptible warm-blooded animal an amount of a composition of claim 128 which is effective against said infection.

137. A method for treating infections caused by susceptible gram-positive bacteria which comprises administering to an infected or susceptible warm-blooded animal an amount of a composition of claim 129 which is effective against said infection.

138. A method for treating infections caused by susceptible gram-positive bacteria which comprises administering to an infected or susceptible warm-blooded animal an amount of a composition of claim 130 which is effective against said infection.

139. A method for treating infections caused by susceptible gram-positive bacteria which comprises administering to an infected or susceptible warm-blooded animal an amount of a composition of claim 131 which is effective against said infection.

140. A method for treating infections caused by Pasteurella species which comprises administering to an infected or susceptible warm-blooded animal an amount of a composition of claim 128 which is effective to treat said infection.

141. A method for treating infections caused by Pasteurella species which comprises administering to an infected or susceptible warm-blooded animal an amount of a composition of claim 129 which is effective to treat said infection.

142. A method for treating infections caused by Pasteurella species which comprises administering to an infected or susceptible warm-blooded animal an amount of a composition of claim 130 which is effective to treat said infection.

143. A method for treating infections caused by Pasteurella species which comprises administering to an infected or susceptible warm-blooded animal an amount of a composition of claim 131 which is effective to treat said infection.

* * * * *

UNITED STATES PATENT AND TRADEMARK OFFICE
CERTIFICATE OF CORRECTION

PATENT NO. : 4,443,436
DATED : April 17, 1984
INVENTOR(S) : Herbert A. Kirst and John E. Toth It is certified that error appears in the above—identified patent and that said Letters Patent is hereby corrected as shown below:

Column 32, line 20, "bonylamino)/aminotylosin" should read -- bonylamino)amino/tylosin --; line 41, "bonylamino)/aminodesmycosin" should read -- bonylamino)amino/desmycosin --.

Column 49, line 21, "20-deoxy-20-/N-(ethoxycarbonyl-N-(ethoxycar-" should read -- 20-deoxy-20-/N-(ethoxycarbonyl)-N-(ethoxycar- --; line 22, "bonylamino)/aminodesmycosin" should read -- bonylamino)amino/desmycosin --.

Column 50, line 20, "$C_1$-$C_4$-" should read -- $C_1$-$C_5$- --.

Column 56, line 12, "pectible" should read --ceptible -- .

Signed and Sealed this

Nineteenth Day of August 1986

[SEAL]

Attest:

Attesting Officer

DONALD J. QUIGG

Commissioner of Patents and Trademarks